United States Patent
Yu et al.

(10) Patent No.: US 10,865,381 B2
(45) Date of Patent: Dec. 15, 2020

(54) MULTI-LINEAGE HEMATOPOIETIC PRECURSOR CELL PRODUCTION BY GENETIC PROGRAMMING

(71) Applicant: FUJIFILM Cellular Dynamics, Inc., Madison, WI (US)

(72) Inventors: Junying Yu, Madison, WI (US); Maksym A. Vodyanyk, Madison, WI (US); Jeffrey Sasaki, Madison, WI (US); Deepika Rajesh, Madison, WI (US); Sarah A. Burton, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 0 days.

(21) Appl. No.: 15/298,931

(22) Filed: Oct. 20, 2016

(65) Prior Publication Data

US 2017/0107492 A1   Apr. 20, 2017

Related U.S. Application Data

(60) Provisional application No. 62/244,101, filed on Oct. 20, 2015, provisional application No. 62/404,470, filed on Oct. 5, 2016.

(51) Int. Cl.
| | |
|---|---|
| *C12N 15/85* | (2006.01) |
| *C12N 5/0783* | (2010.01) |
| *C12N 5/0784* | (2010.01) |
| *C12N 5/0789* | (2010.01) |
| *C12N 5/0781* | (2010.01) |
| *C12N 15/86* | (2006.01) |

(52) U.S. Cl.
CPC ......... *C12N 5/0636* (2013.01); *C12N 5/0635* (2013.01); *C12N 5/0637* (2013.01); *C12N 5/0638* (2013.01); *C12N 5/0639* (2013.01); *C12N 5/0646* (2013.01); *C12N 5/0647* (2013.01); *C12N 15/85* (2013.01); *C12N 15/86* (2013.01); *C12N 2500/38* (2013.01); *C12N 2500/90* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/22* (2013.01); *C12N 2501/2303* (2013.01); *C12N 2501/2306* (2013.01); *C12N 2501/2307* (2013.01); *C12N 2501/25* (2013.01); *C12N 2501/26* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2501/998* (2013.01); *C12N 2501/999* (2013.01); *C12N 2506/025* (2013.01); *C12N 2506/03* (2013.01); *C12N 2506/09* (2013.01); *C12N 2506/11* (2013.01); *C12N 2506/45* (2013.01); *C12N 2510/00* (2013.01); *C12N 2533/50* (2013.01); *C12N 2840/20* (2013.01)

(58) Field of Classification Search
CPC .. C12N 5/0636; C12N 5/0639; C12N 5/0646; C12N 5/0647; C12N 15/85
See application file for complete search history.

(56) References Cited

U.S. PATENT DOCUMENTS

| | | | |
|---|---|---|---|
| 6,482,926 B1 | 11/2002 | Thomas et al. | |
| 7,259,011 B2 | 8/2007 | Paul et al. | |
| 8,323,966 B2 | 12/2012 | Lebkowski et al. | |
| 9,040,039 B2 | 5/2015 | Klimanskaya | |
| 9,040,770 B2 | 5/2015 | Klimanskaya | |
| 2008/0299095 A1 | 12/2008 | Humphries et al. | |
| 2010/0105137 A1 | 4/2010 | Takahashi et al. | |
| 2013/0149284 A1 | 6/2013 | Malcuit et al. | |
| 2013/0196369 A1 | 8/2013 | Hikita et al. | |
| 2013/0224156 A1 | 8/2013 | Takahashi et al. | |
| 2013/0280809 A1* | 10/2013 | Efe ............... | C12N 5/0602 435/467 |
| 2014/0220681 A1 | 8/2014 | Valamehr et al. | |
| 2015/0086512 A1 | 3/2015 | Malcuit et al. | |
| 2015/0159134 A1 | 6/2015 | Choudhray et al. | |
| 2015/0175964 A1 | 6/2015 | Clegg et al. | |
| 2017/0067017 A1 | 3/2017 | Meyer et al. | |
| 2017/0107492 A1 | 4/2017 | Yu et al. | |

(Continued)

FOREIGN PATENT DOCUMENTS

| | | |
|---|---|---|
| WO | WO 2011-063005 | 5/2011 |
| WO | WO 2012-109208 | 8/2012 |

(Continued)

OTHER PUBLICATIONS

Takeda et al. Cancer Res 66:6628-6637, 2006.*

(Continued)

*Primary Examiner* — Marcia S Noble
(74) *Attorney, Agent, or Firm* — Parker Highlander PLLC

(57) ABSTRACT

The present disclosure generally regards methods and compositions for providing multi-lineage hematopoietic precursor cells from pluripotent stem cells (PSCs). The PSCs comprise an expression construct encoding an ETS/ERG gene, GATA2 and HOXA9. Also provided are methods for providing hematopoietic stem cells capable of long-term engraftment in mammals, such as humans. Further provided are therapeutic compositions including the provided hematopoietic stem cells and precursors of hematopoietic cells, and methods of using such for the treatment of subjects.

35 Claims, 8 Drawing Sheets

(56) References Cited

U.S. PATENT DOCUMENTS

| | | |
|---|---|---|
| 2018/0258388 A1 | 9/2018 | Ando et al. |
| 2019/0169569 A1 | 6/2019 | Bharti et al. |

FOREIGN PATENT DOCUMENTS

| | | |
|---|---|---|
| WO | WO 2013-039792 | 3/2013 |
| WO | WO 2013-114360 | 8/2013 |
| WO | WO 2014-121077 | 8/2014 |
| WO | WO 2014-153069 | 9/2014 |
| WO | WO 2015-054526 | 4/2015 |
| WO | WO 2015-087231 | 6/2015 |

OTHER PUBLICATIONS

Gonzalez et al. PNAS 106(22):8918-8922, 2009 (Year: 2009).*
Amedola et al. Nature Biotechnology 23(1):108-116, 2005 (Year: 2005).*
Miskaia and Ryan. BioMed Research International 2013. Article ID 291790 pp. 1-12. (Year: 2013).*
Vacca et al. PNAS 108(6):2402-2407, 2011 (Year: 2011).*
SBI. pCDH cDNA cloning and expression lentivectors user manual. pp. 1-20, 2013 (Year: 2013).*
Clontech. Tet-Off Advanced Inducible Gene Expression System User Manual. pp. 1-27, 2007 (Year: 2007).*
Batta et al., "Direct Reprogramming of Murine Fibroblasts to Hematopoietic Progenitor Cells," Cell Rep., 9(5):1871-1884, 2014.
Doulatov et al., "Induction of multipotential hematopoietic progenitors from human pluripotent stem cells via respecification of lineage-restricted precursors," Cell Stem Cell, 13(4):459-470, 2013.
Ebina et al., "Transcription factor-mediated reprogramming toward hematopoietic stem cells," EMBO Journal, 34(6):694-709, 2015.
Elcheva et al., "Direct induction of haematoendothelial programs in human pluripotent stem cells by transcriptional regulators," Nat Commun, 5:4372, 2014.
Kitajima et al., "In vitro generation of HSC-like cells from murine ESCs/iPSCs by enforced expression of LIM-homeobox transcription factor Lhx2," Blood, 117(14):3748-3758, 2011.
Kyba et al., "HoxB4 confers definitive lymphoid-myeloid engraftment potential on embryonic stem cell and yolk sac hematopoietic progenitors," Cell, 109(1):29-37, 2002.
McIntosh et al., "Nonirradiated NOD,B6.SCID Il2rγ-/-Kit(W41/W41) (NBSGW) mice support multilineage engraftment of human hematopoietic cells," Stem Cell Reports, 4(2):171-180, 2015.
PCT International Search Report and Written Opinion issued in International Application No. PCT/US2016/057893, dated Dec. 6, 2016.
Pereira et al., "Induction of a Hemogenic Program in Mouse Fibroblasts," Cell Stem Cell, 13(2):205-218, 2013.
Ramos-Mejia et al., "HOXA9 promotes hematopoietic commitment of human embryonic stem cells," Blood, 124(20)Suzuki :3065-3075, 2014.
Riddell et al., "Reprogramming committed murine blood cells to induced hematopoietic stem cells with defined factors," Cell, 157(3):549-564, 2014.
Sandler et al., "Reprogramming human endothelial cells to haematopoietic cells requires vascular induction," Nature, 511(7509):312-318, 2014.
Suzuki et al., "Generation of Engraftable Hematopoietic Stem Cells From Induced Pluripotent Stem Cells by Way of Teratoma Formation," Mol Ther., 21(7):1424-1431, 2013.
Vo et al., "De novo generation of HSCs from somatic and pluripotent stem cell sources," Blood, 125(17):2641-2648, 2015.
Bharti et al., "The new paradigm: retinal pigment epithelium cells generated from embryonic or induced pluripotent stem cells." Pigment Cell Melanoma Res. 24: 21-34 (published online Sep. 15, 2010).
Bharti et al., U.S. Appl. No. 61/759,988, entitled "Method for generating retinal pigment epithlium (RPE) cells from induced pluripotent stem cells (IPSCs)," filed Feb. 1, 2013.
Buckholz et al., "Derivation of functional retinal pigment epithelium from induced pluripotent stem cells," Stem Cells, 29(9): 1391-1404, 2011.
Klimanskaya et al., "Derivation and comparative assessment of retinal pigment epithelium from human embryonic stem cells using transcriptomics," Cloning and Stem Cells 6(3): 217-245 (Nov. 3, 2004).
Lakowski et al., "Effective transplantation of photoreceptor precursor cells selected via cell surface antigen expression," Stem Cells, 29.9: 1391-1404, 2011.
Mandai et al., "Use of lectins to enrich mouse ES-derived retinal progenitor cells for the purpose of transplantation therapy," Cell Transplantation, 19.1:9-19, 2010.
PCT International Search Report and Written Opinion issued in International Application No. PCT/US2016/050543, dated Dec. 5, 2016.
PCT International Search Report and Written Opinion issued in International Application No. PCT/US2016/050554, dated Nov. 28, 2016.
Rowland et al., "Differemiation of human pluripotent stem cells to retinal pigmented epithelium in defined conditions using purified extracellular matrix proteins." Journal of Tissue Engineering and Regenerative Medicine 7: 642-653 (published online Apr. 18, 2012).
Sundberg et al., "CD marker expression profiles of human embryonic stem cells and their neural derivatives, determined using flow-cytometric analysis, reveal a novel CD marker for exclusion of pluripotent stem cells," Stem Cell Research, 2:113-124, 2009.
Thomson et al., "Human embryonic stem cell and embryonic germ cell lines," Trends in Biotechnology 18.2 (2000): 53-57.
Van der Jeught et al., "The combination of inhibitors of EGF/MEK/Erk and GSK3β signaling increases the number of OCT3/4-and NANOG-positive cells in the human inner cell mass, but does not improve stem cell derivation" Stem Cells and Development 22(2): 296-306 (published online Jul. 11, 2012).
Vugler et al., "Elucidating the phenomenon of HESC-derived RPE: anatomy of cell genesis, expansion and retinal transplantation." Experimental Neurology 214: 347-361 (published online Sep. 27, 2008).
Young et al., "Human Pluripotent and Progenitor Cells Display Cell Surface Cluster Differentiation Markers CD10, CD13, CD56 and MHC Class-I", Proceedings of the Society of Experimental Biology and Medicine, 1999, vol. 221, No. 1, pp. 63-71. (Year: 1999).

* cited by examiner

MULTI-LINEAGE HEMATOPOIETIC PRECURSOR CELL PRODUCTION BY GENETIC PROGRAMMING

The present application claims the priority benefit of U.S. Provisional Applications Ser. No. 62/244,101, filed Oct. 20, 2015, and Ser. No. 62/404,470, filed Oct. 5, 2016, the entire contents of both applications being hereby incorporated by reference.

BACKGROUND OF THE INVENTION

1. Field of the Invention

The present invention relates generally to the fields of molecular biology, stem cells, and differentiated cells. More particularly, it concerns programming of pluripotent stem cells (PSCs) toward specific cell lineages, particularly hematopoietic cells and precursors of hematopoietic cells.

2. Description of Related Art

Hematopoietic stem cells (HSCs) are the only cells with the capacity to self-renew for life, differentiate into all blood cell types, and reconstitute the entire hematopoietic system upon transplantation. These cells, along with their terminally differentiated derivative cell types such as erythrocytes, platelets, granulocytes, and lymphoid cells, have well established therapeutic applications in treating various blood disorders and, more recently, cancers. However, the limited availability of HSCs from HLA-matched living donors puts a major restriction on their wide use in clinics. Considerable efforts, thus, have been made to derive HSCs from alternative cell types.

One approach to derive HSCs from alternative cell types is to transdifferentiate non-HSC somatic cell types into HSCs. Various combinations of transgenes have been used to transdifferentiate mouse fibroblasts into non-engraftable hematopoietic progenitors (Pereira et al., 2013; Batta et al., 2014). However, this approach is limited due to the number of starting primary cells along with a low transdifferentiation efficiency. Thus, there is a lack of methods that provide an unlimited supply of hematopoietic precursor cells that have the potential for long-term engraftment.

Human embryonic stem cells (ESCs) and induced pluripotent stem cells (iPSC) are capable of unlimited proliferation in vitro, while retaining the potential to differentiate into all somatic cell types. Human ESC and iPSCs, therefore, could potentially provide an unlimited supply of patient-specific HSCs and functional blood cells for both in vitro and in vivo applications. The differentiation of human PSCs to cells of hematopoietic lineage in vitro recapitulates normal in vivo development including stages of mesoderm induction and specification of multipotent hematopoietic precursors. Thus, numerous methods have been developed to differentiate human PSCs into hematopoietic lineages through forward programming.

However, no method is currently available to allow robust generation of HSCs that are capable of efficient myeloid and lymphoid differentiation and long-term engraftment from PSCs, mainly due to the complex nature of hematopoietic ontogeny. In one method, overexpression of transgenes such as HoxB4 and Lhx2 for hematopoietic differentiation of mouse PSCs has been shown to generate engraftable HSC-like cells (Kyba et al. 2002; Kitajima et al., 2011). These transgenes, however, failed to generate HSCs from human PSCs. In another method, Doulatov et al. reported that a combination of ERG, HOXA9, RORA, SOX4 and MYB transgenes in human PSCs enabled the production of hematopoietic progenitors that were capable of myeloid and erythroid differentiation (Doulatov et al., 2013). However, this method only generated cells capable of short-term engraftment that relied on continued transgene expression. Thus, although genetic programming proves to be a very promising approach, there is a lack of methods that allow robust generation of hematopoietic precursor cells capable of lymphoid and myeloid potential and long-term engraftment from human PSCs in vitro.

SUMMARY OF THE INVENTION

Embodiments of the present disclosure provide methods for the efficient programming of human pluripotent stem cells into multi-lineage hematopoietic progenitors. In a first embodiment, there is provided an in vitro method for producing hematopoietic precursor cells (HPCs) from pluripotent stem cells comprising providing pluripotent stem cells (PSCs) comprising at least one expression construct encoding hematopoietic precursor programming genes, wherein the hematopoietic precursor programming genes comprise an ETS/ERG gene, GATA2, and HOXA9, and culturing the pluripotent stem cells under conditions such that the hematopoietic precursor programming genes are expressed, thereby producing hematopoietic precursor cells. In certain aspects, the HPCs are capable of differentiating into myeloid and lymphoid lineages. In some aspects, the pluripotent stem cells are embryonic stem cells (ESCs) or induced pluripotent stem cells (iPSCs). In certain aspects, the pluripotent stem cells are human.

In certain aspects, the expression construct is a transposon- or episomal-based expression construct. In some aspects, the hematopoietic precursor programming genes are under the control of a single promoter. In particular aspects, the single promoter is an inducible promoter. In a specific aspect, the inducible promoter is a tetracycline-inducible promoter.

In further aspects, the method for producing hematopoietic precursor cells further comprises culturing the HPCs under conditions such that the hematopoietic precursor programming genes are not expressed. In certain aspects, the HPCs are cultured in the absence of stromal cells. In some aspects, the HPCs are cultured in serum free or defined medium. In certain aspects, the HPCs can be differentiated into two or more cell types selected from the group consisting of plasma cell, natural killer cell, macrophage, mast cell, megakaryocyte, erythrocyte, granulocyte, lymphocyte, monocyte, leukocyte, and thrombocyte. In certain aspects, the lymphocyte is a B lymphocyte and/or a T lymphocyte.

In some aspects, the culturing of the pluripotent stem cells under conditions such that the hematopoietic precursor programming genes are expressed is about four to about ten days.

In certain aspects, the HPCs express one or more hematopoietic precursor markers. In some aspects, the hematopoietic precursor markers are selected from the group consisting of CD43, CD33, CD34, CD45, CD235a, and CD41a. In particular aspects, the one or more hematopoietic precursor markers are selected from the group consisting of CD43, CD45, and CD34. In some aspects, the HPCs are immature HPCs. In certain aspects, the immature HPCs express CD34 and CD43. In some aspects, at least 50 percent of the HPCs are immature HPCs, such as at least 55, 60, 65, 70, 75, 80, 90, 95, 96, 97, 98, or 99 percent of the HPCs. In further aspects, at least 70 percent of the HPCs are immature HPCs. In even further aspects, at least 90 percent of the HPCs are immature HPCs.

In certain aspects, the ETS/ERG gene is ERG (v-ets erythroblastosis virus E26 oncogene homolog), ETV2 (ets variant 2), FLI-1 (Friend leukemia virus integration 1), ELK3 (ETS domain-containing protein), ETS1 (C-ets-1), or ETS2 (C-ets-2). In particular aspects, the ETS/ERG gene is ERG or ETV2.

In some aspects, the hematopoietic precursor programming genes comprise ERG, GATA2, and HOXA9. In other aspects, the hematopoietic precursor programming genes comprise ETV2, GATA2, and HOXA9.

In certain aspects, the hematopoietic precursor programming genes are fused to a targeting sequence. For example, the targeting sequence is NUP98 or a homeodomain thereof. In certain aspects, hematopoietic precursor programming genes comprise ERG, GATA2, HOXA9, NUP98-HOXA9 and NUP98-HOXA10. In other aspects, the hematopoietic precursor programming genes comprise ETV2, GATA2, HOXA9, NUP98-HOXA9 and NUP98-HOXA10.

In further aspects, the PSCs comprising at least one expression construct encoding hematopoietic precursor programming genes further comprise at least one additional expression construct encoding one or more hematopoietic stem cell programming genes.

In even further aspects, the in vitro method for producing hematopoietic precursor cells from pluripotent stem cells further comprises culturing the HPCs under conditions such that the one or more hematopoietic stem cell programming genes are expressed, thereby producing hematopoietic stem cells (HSCs) capable of long-term engraftment in a mammal. In certain aspects, the mammal is a human. In some aspects, the one or more hematopoietic stem cell programming genes are selected from the group consisting of BCL2, BEND4, BMI1, CIITA, EGR3, ETV6, EZH1, EZH2, FOXL1, HIF3A, HLF, HMGA2, HOXA9, HOXA10, HOXA3, HOXA4, HOXA5, HOXA6, HOXA7, HOXB3, HOXB6, HSF5, KLF2, KLF4, MECOM, MEIS1, MIR29A, MIR29B1, MSI2, MYB, MYCN, NKX2-3, NR4A2, PEG3, PRDM12, PRDM16, RBAK, RUNX1, RUNX3, SETBP1, SOX17, SOX8, TFEC, ZBTB14, ZBTB20, ZMAT1, ZNF131, ZNF134, ZNF136, ZNF256, ZNF26, ZNF300, ZNF337, ZNF350, ZNF414, ZNF662, ZNF667, and ZNF682. In certain aspects, the one or more hematopoietic stem cell programming genes are selected from the group consisting HMGA2, MYCN, NR4A2, SOX17, TFEC, MEIS1, HOXA4, ZNF414, KLF4, ZNF131, BCL2, ETV6, ZNF350, RBAK, HOXA6, HOXB6, HOXA7, ZNF300, ZNF682, and MSI2. In particular aspects, the one or more hematopoietic stem cell programming genes are selected from the group consisting of HMGA2, MYCN, NR4A2, SOX17, TFEC, MEIS1, HOXA4, ZNF414, KLF4, ZNF131, BCL2, ETV6, ZNF350, and RBAK.

In some aspects, expression of the one or more hematopoietic stem cell programming genes is constitutive in the HPCs. In certain aspects, expression of the one or more hematopoietic stem cell programming genes is essentially silenced in the pluripotent stem cells.

In certain aspects, the hematopoietic stem cell programming genes are fused to a targeting sequence. In particular aspects, the targeting sequence is NUP98 or a homeodomain thereof.

In another embodiment, there is provided an in vitro method for producing hematopoietic precursor cells from pluripotent stem cells comprising providing pluripotent stem cells (PSCs) comprising an expression construct encoding ERG, GATA2, and HOXA9 under the control of a single promoter, and culturing the pluripotent stem cells under conditions such that ERG, GATA2, and HOXA9 are expressed, thereby producing hematopoietic precursor cells (HPCs).

In yet another embodiment, there is provided an in vitro method for producing hematopoietic stem cells (HSCs) from pluripotent stem cells comprising providing pluripotent stem cells (PSCs) comprising an expression construct encoding ERG, GATA2, and HOXA9 under the control of a single promoter and at least a second expression construct encoding one or more hematopoietic stem cell programming genes, culturing the pluripotent stem cells under conditions such that ERG, GATA2, HOXA9 and the one or more hematopoietic stem cell programming genes are expressed, thereby producing HSCs capable of long-term engraftment in a mammal.

In a further embodiment, there is provided an expression construct encoding hematopoietic precursor programming genes, wherein the programming genes comprise an ETS/ERG gene, GATA2 and HOXA9. In some aspects, the construct is a transposon- or episomal-based expression construct. In certain aspects, the hematopoietic precursor programming genes are under the control of a single promoter. In some aspects, the single promoter is an inducible promoter. In particular aspects, the inducible promoter is a tetracycline-inducible promoter. In some aspects, the ETS/ERG gene is ERG (v-ets erythroblastosis virus E26 oncogene homolog), ETV2 (ets variant 2), FLI-1 (Friend leukemia virus integration 1), ELK3 (ETS domain-containing protein), ETS1 (C-ets-1), or ETS2 (C-ets-2). In specific aspects, the ETS/ERG gene is ERG or ETV2. In some aspects, the hematopoietic precursor programming genes comprise ERG, GATA2, and HOXA9. In other aspects, the hematopoietic precursor programming genes comprise ETV2, GATA2, and HOXA9. In certain aspects, the hematopoietic precursor programming genes are fused to a target sequence. In particular aspects, the targeting sequence is NUP98 or a homeodomain thereof. In some aspects, the hematopoietic precursor programming genes comprise ERG, GATA2, HOXA9, NUP98-HOXA9 and NUP98-HOXA10. In other aspects, hematopoietic precursor programming genes comprise ETV2, GATA2, HOXA9, NUP98-HOXA9 and NUP98-HOXA10.

In another embodiment, there is provided a cell comprising the expression construct encoding hematopoietic precursor programming genes, wherein the programming genes comprise an ETS/ERG gene, GATA2, and HOXA9.

In yet another embodiment, there is provided an expression construct encoding one or more hematopoietic stem cell programming genes. In particular aspects, the one or more hematopoietic stem cell programming genes are selected from the group consisting of BCL2, BEND4, BMI1, CIITA, EGR3, ETV6, EZH1, EZH2, FOXL1, HIF3A, HLF, HMGA2, HOXA9, HOXA10, HOXA3, HOXA4, HOXA5, HOXA6, HOXA7, HOXB3, HOXB6, HSF5, KLF2, KLF4, MECOM, MEIS1, MIR29A, MIR29B1, MSI2, MYB, MYCN, NKX2-3, NR4A2, PEG3, PRDM12, PRDM16, RBAK, RUNX1, RUNX3, SETBP1, SOX17, SOX8, TFEC, ZBTB14, ZBTB20, ZMAT1, ZNF131, ZNF134, ZNF136, ZNF256, ZNF26, ZNF300, ZNF337, ZNF350, ZNF414, ZNF662, ZNF667, and ZNF682. In certain aspects, the one or more hematopoietic stem cell programming genes are selected from the group consisting HMGA2, MYCN, NR4A2, SOX17, TFEC, MEIS1, HOXA4, ZNF414, KLF4, ZNF131, BCL2, ETV6, ZNF350, RBAK, HOXA6, HOXB6, HOXA7, ZNF300, ZNF682, and MSI2. In particular aspects, the one or more hematopoietic stem cell programming genes are selected from the group consisting of HMGA2, MYCN, NR4A2, SOX17, TFEC, MEIS1, HOXA4, ZNF414, KLF4, ZNF131, BCL2, ETV6, ZNF350, and RBAK. In certain aspects, the one or more hematopoietic stem cell programming genes are under the control of a cytomegalovirus (CMV) promoter. In some aspects, the hematopoietic stem cell programming genes are fused to a targeting sequence. In one specific aspects, the targeting sequence is NUP98 or a homeodomain thereof.

In a further embodiment, there is provided a cell comprising the expression construct encoding one or more hematopoietic stem cell programming genes.

In yet a further embodiment, there is provided a hematopoietic stem cell, differentiated in vitro from a human pluripotent stem cell, capable of engrafting in the bone marrow of a mammal and producing differentiated human blood cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
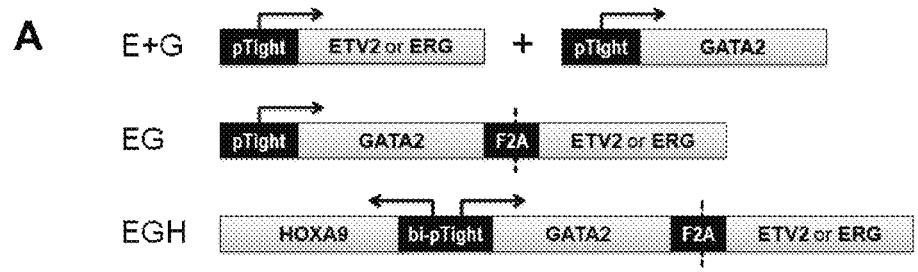
FIGS. 1A-1F. Linked co-expression of ETV2/ERG, GATA2 and HOXA9 efficiently programs human PSCs to immature CD34+ hematopoietic progenitors. (A) Tested configurations of programming genes ETV2/ERG, GATA2 and HOXA9 are shown. (B) E+G, EG and EGH inductive gene configurations were tested using human PSCs engineered to constitutively express rtTET protein for the doxycycline (DOX)-inducible gene expression. (C) Absolute cell counts in day 8-induced cultures in both ETV2- and ERG-based gene configurations. (D) The expansion and differentiation potentials of day 8 DOX-induced cells in co-culture with MS5 stromal cells are shown. (E) Absolute counts of total $CD43^+$ and immature $CD43^+$ $CD34^+$ cells following a 2 week co-culture with MS5 stromal cells. (F) Multilineage colony-forming potential was detected in EGH-induced cells following 2 weeks co-culture with MS5 stroma.

The present disclosure overcomes several major problems with current technologies by providing methods and compositions for producing multi-lineage hematopoietic precursor cells from pluripotent stem cells (PSCs). In particular, the multi-lineage hematopoietic precursor cells can be programmed to hematopoietic stem cells capable of long-term engraftment. The inventors have discovered that one way of achieving multi-lineage hematopoietic precursor cells is to transfect PSCs with one or more expression vectors that effect the expression of at least three specific genes whose expression moderates a 'forward programming' of the PSCs into multi-lineage hematopoietic precursor cells. Notably, the methods of the present disclosure apply to any type of pluripotent stem cells, including for example embryonic stem cells or induced pluripotent stem cells. In particular, the multi-lineage hematopoietic precursors have the potential to efficiently differentiate into myeloid and lymphoid lineage cells.

Preferably, the hematopoietic programming genes are ETV2 or ERG, GATA2 and HOXA9. In particular aspects, the hematopoietic programming genes are under the control of a single promoter, such as an inducible promoter. Generally, the hematopoietic programming genes are expressed for only a period of time sufficient to forward program the PSCs into hematopoietic precursor cells.

Once the immature multi-lineage hematopoietic precursors are formed, the inventors have discovered that it is preferred to take an additional step or steps in order to render hematopoietic stem cells capable of long-term engraftment. In one method, the PSCs are transfected with one or more additional expression construct(s) that encode one or more hematopoietic stem cell programming gene(s) whose expression enables the multi-lineage hematopoietic precursors to be stably engrafted in vivo. In certain aspects, the hematopoietic stem cell programming gene(s) for long-term engraftment are expressed in the immature hematopoietic precursor cells, but not expressed in the PSCs.

Thus, the methods of the present disclosure provide unlimited numbers of multi-lineage hematopoietic precursors and hematopoietic stem cells for a wide range of applications such as stable transplantation of the hematopoietic precursors in vivo, screening of compounds in vitro, and elucidating the mechanisms of hematological diseases and injuries.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present methods may also use genetically engineered replication origin of EBV, such as by insertion or mutation of individual elements, as specifically described in Lindner et al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct3/4), Sox2, c-Myc, Klf4, Nanog, and Lin28. In some embodiments, somatic cells are reprogrammed by expressing at least two reprogramming factors, at least three reprogramming factors, at least four reprogramming factors, or at least five reprogramming factors to reprogram a somatic cell to a pluripotent stem cell.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

The term "hematopoietic precursor programming gene" is a gene that, when expressed alone or in combination with another programming gene, is capable of forward programming pluripotent stem cells into hematopoietic precursor cells capable of producing lymphoid and myeloid lineage cells.

The term "hematopoietic stem cell programming gene" is a gene that, when expressed alone or in combination with another programming gene, is capable of programming hematopoietic stem cells capable of long-term engraftment in combination with hematopoietic precursor programming genes.

As used herein, "2A sequences" refer to short peptides that allow co-expression of multiple proteins from a single vector. These small peptides can be introduced as a linker between two proteins, allowing autonomous intraribosomal self-processing of polyproteins (See e.g., de Felipe. *Genetic Vaccines and Ther.* 2:13 (2004); deFelipe et al. *Traffic* 5:616-626 (2004)). Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A) as described in U.S. Patent Publication No. 20070116690, incorporated herein by reference.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

The "multi-lineage construct" is used herein to refer to a construct that encodes at least three hematopoietic programming genes including an ETS gene, a homeobox gene and a hematopoietic development gene. One exemplary construct encodes ETV2 or ERG, GATA2 and HOXA9.

As used herein, the term "engraftment" with respect to hematopoietic stem cells or hematopoietic precursor cells means that cells which are introduced into a recipient are localized in the bone marrow of the recipient and can provide long term reconstitution of both myeloid and lymphoid cell lineages in that recipient.

"Long-term engraftment" is defined herein as the stable transplantation of cells such as the hematopoietic precursor cells provided by the methods herein into a recipient such that the transplanted cells persist in the host blood and/or bone marrow more than 10 weeks, preferably more than 20 weeks. In addition, long-term engraftment can be characterized by the persistence of transplantation cells in serially transplanted mice.

II. CELLS INVOLVED IN HEMATOPOIETIC CELL PROGRAMMING

In certain embodiments, there are disclosed methods and compositions for providing multi-lineage hematopoietic precursor cells from pluripotent stem cells. The pluripotent stem cells may be stem cells including but are not limited to, induced pluripotent stem cells and embryonic stem cells.

The pluripotent stem cells used in the present methods to produce hematopoietic precursor cells are characterized by the ability to renew themselves through mitotic cell division and the ability to differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin or intestinal tissues.

In particular aspects, the pluripotent stem cells used herein are human embryonic stem cells (ESCs) or induced pluripotent stem cells (iPSCs) which are capable of long-term proliferation in vitro, while retaining the potential to differentiate into all cell types of the body, including the hematopoietic precursor cells of the present disclosure. Thus, these cells could potentially provide an unlimited supply of patient-specific functional hematopoietic cells for both drug development and therapeutic uses. Certain aspects of the present disclosure provide multi-lineage hematopoietic precursor cells by forward programming from human PSCs such as ESCs and iPSCs via expression of a combination of programming genes important for hematopoietic cell differentiation/function.

A. Embryonic Stem Cells

In certain aspects, the pluripotent stem cells as embryonic stem cells (ESCs). ES cells are derived from the inner cell mass of blastocysts and have a high in vitro differentiating capability. ES cells can be isolated by removing the outer trophectoderm layer of a developing embryo, then culturing the inner mass cells on a feeder layer of non-growing cells. The replated cells can continue to proliferate and produce new colonies of ES cells which can be removed, dissociated, replated again and allowed to grow. This process of "subculturing" undifferentiated ES cells can be repeated a number of times to produce cell lines containing undifferentiated ES cells (U.S. Pat. Nos. 5,843,780; 6,200,806; 7,029,913). ES cells have the potential to proliferate while maintaining their pluripotency. For example, ES cells are useful in research on cells and on genes which control cell differentiation. The pluripotency of ES cells combined with genetic manipulation and selection can be used for gene analysis studies in vivo via the generation of transgenic, chimeric, and knockout mice.

Methods for producing mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be produced or derived from a zygote or blastocyst-staged mammalian embryo produced by the fusion of a sperm and egg cell, nuclear transfer, pathogenesis, or the reprogramming of chromatin and subsequent incorporation of the reprogrammed chromatin into a plasma membrane to produce an embryonic cell by previously described methods (Thomson and Marshall, 1998; Reubinoff et al., 2000). In one method, human blastocysts are exposed to anti-human serum, and trophectoderm cells are lysed and removed from the inner cell mass which is cultured on a feeder layer of mouse embryonic fibroblasts. Further, clumps of cells derived from the inner cell mass are chemically or mechanically dissociated, replated, and colonies with undifferentiated morphology are selected by micropipette, dissociated, and replated. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as MATRIGEL™ or laminin in the presence of "conditioned" medium containing basic fibroblast growth factor (Xu et al., 2001).

ES cells can also be derived from other organisms including rhesus monkey and marmoset by previously described methods (Thomson, and Marshall, 1998; Thomson et al., 1995; Thomson and Odorico, 2000; U.S. Pat. No. 5,843,780), as well as from established mouse and human cell lines. For example, established human ES cell lines include MAOI, MA09, ACT-4, HI, H7, H9, H13, H14 and ACT30. As a further example, mouse ES cell lines that have been established include the CGR8 cell line established from the inner cell mass of the mouse strain 129 embryos, and cultures of CGR8 cells can be grown in the presence of LIF without feeder layers.

ES stem cells can be detected by protein markers including transcription factor Oct4, alkaline phosphatase (AP), stage-specific embryonic antigen SSEA-1, stage-specific embryonic antigen SSEA-3, stage-specific embryonic antigen SSEA-4, transcription factor NANOG, tumor rejection antigen 1-60 (TRA-1-60), tumor rejection antigen 1-81 (TRA-1-81), SOX2, or REX1.

B. Induced Pluripotent Stem Cells

In other aspects, the pluripotent stem cells used herein are induced pluripotent stem (iPS) cells, commonly abbreviated iPS cells or iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. The use of iPSCs circumvents most of the ethical and practical problems associated with large-scale clinical use of ES cells, and patients with iPSC-derived autologous transplants may not require lifelong immunosuppressive treatments to prevent graft rejection.

With the exception of germ cells, any cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein.

Somatic cells can be reprogrammed to produce induced pluripotent stem cells (iPSCs) using methods known to one of skill in the art. One of skill in the art can readily produce induced pluripotent stem cells, see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,268,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized.

Mouse and human cDNA sequences of these nuclear reprogramming substances are available with reference to the NCBI accession numbers mentioned in WO 2007/069666 and U.S. Pat. No. 8,183,038, which are incorporated herein by reference. Methods for introducing one or more reprogramming substances, or nucleic acids encoding these reprogramming substances, are known in the art, and disclosed for example, in U.S. Pat. Nos. 8,268,620, 8,691,574, 8,741,648, 8,546,140, in published U.S. Pat. Nos. 8,900,871 and 8,071,369, which both are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used with the present methods.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™/Essential 8™ medium (Chen et al., 2011).

Plasmids have been designed with a number of goals in mind, such as achieving regulated high copy number and avoiding potential causes of plasmid instability in bacteria, and providing means for plasmid selection that are compatible with use in mammalian cells, including human cells. Particular attention has been paid to the dual requirements of plasmids for use in human cells. First, they are suitable for maintenance and fermentation in *E. coli*, so that large amounts of DNA can be produced and purified. Second, they are safe and suitable for use in human patients and animals. The first requirement calls for high copy number plasmids that can be selected for and stably maintained relatively easily during bacterial fermentation. The second requirement calls for attention to elements such as selectable markers and other coding sequences. In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. No. 6,103,470; U.S. Pat. Nos. 7,598,364; 7,989,425; and 6,416,998, which are incorporated herein by reference.

An episomal gene delivery system can be a plasmid, an Epstein-Barr virus (EBV)-based episomal vector (U.S. Pat. No. 8,546,140), a yeast-based vector, an adenovirus-based vector, a simian virus 40 (SV40)-based episomal vector, a bovine papilloma virus (BPV)-based vector, or a lentiviral vector. A viral gene delivery system can be an RNA-based or DNA-based viral vector (PCT/JP2009/062911).

C. Embryonic Stem Cells Derived by Somatic Cell Nuclear Transfer

Pluripotent stem cells for producing the hematopoietic precursor cells could also be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo.

III. HEMATOPOIETIC PRECURSOR CELL PROGRAMMING FACTORS

A. Hematopoietic Precursor Programming Factors

Certain aspects of the present disclosure provide constructs encoding hematopoietic precursor programming genes for programming PSCs to multi-lineage hematopoietic precursor cells. The multi-lineage hematopoietic precursor cells of the present disclosure could be produced directly from pluripotent stem cells by modifying the PSCs to express at least three hematopoietic precursor programming genes such as an ETS gene, a hematopoietic development gene, and a homoebox gene. The at least three hematopoietic precursor programming genes can be encoded by one or more multi-lineage constructs.

The hematopoietic precursor programming gene can be fused to a sequence known in the art for expansion of the hematopoietic precursor cells (U.S. Patent Publication No. US20080299095, incorporated herein by reference). An exemplary sequence is NUP98 or a homeodomain thereof.

1. ETS Genes

The multi-lineage construct(s) encodes at least one gene from the E26 transformation-specific (ETS) family of transcription factors. All ETS family members are identified through a highly conserved DNA binding domain, the ETS domain, which is a winged helix-turn-helix structure that binds to DNA sites with a central GGA(A/T) DNA sequence. As well as DNA-binding functions, evidence suggests that the ETS domain is also involved in protein-protein interactions. The ETS family is present throughout the body and is involved in a wide variety of functions including the regulation of cellular differentiation, cell cycle control, cell migration, cell proliferation, apoptosis (programmed cell death) and angiogenesis. The members of this family of genes have been implicated in the development of different tissues as well as cancer progression.

The ETS gene may be any gene in the ETS family which is divided into 12 subfamilies including ELF, ELG, ERG, ERF, ESE, ETS, PDEF, PEA3, ER71, SPI, TCF, and TEL. For example, the ETS could be ERG (v-ets erythroblastosis virus E26 oncogene homolog; Accession No. NM_001136154), ETV2 (ets variant 2; Accession No. NC_000019.10), FLI-1 (Friend leukemia virus integration 1; Accession No. NM_001167681), ELK3 (ETS domain-containing protein; Accession No. NM_001303511), ETS1 (C-ets-1; Accession No. NM_001143820), ETS2 (C-ets-2; Accession No. NM_001256295), E74-like factor 1 (ELF1; Accession No. M_001145353), E74-like factor 2 (ELF2; Accession No. NM_001276457), ETS-related transcription factor (ELF4; Accession No. NM_001127197), Ets variant 3 (ETV3; Accession No. NM_001145312), or Transcription factor PU.1 (SPI1; Accession No. NM_001080547). In particular, the ETS gene could be the endothelial differentiation factor called ERG, which is also known as: transcriptional regulator ERG, ets-related transforming protein ERG, TMPRSS2-ERG prostate cancer specific, v-ets erythroblastosis virus E26 oncogene like, v-ets avian erythroblastosis virus E26 oncogene related, or transforming protein ERG. In some embodiments, the ETS gene is a particular isoform of ERG, such as ERG isoform 2 (ERG-2) (Accession No. NM_004449) or ERG isoform 3 (ERG-3) (Accession No. NM_001136154). In particular embodiments, the ETS gene is ETV2.

2. Hematopoietic Development Genes

The multi-lineage construct(s) also encodes at least one hematopoietic development gene. The hematopoietic development gene could be any gene that induces hematopoietic development. Non-limiting examples of the hematopoietic development gene include GFI1 (growth factor independent 1 transcription repressor; Accession No. NM_001127215), GFI1B (growth factor independent 1B transcription repressor; Accession No. NM_001135031), TAL1 (T-cell acute lymphocytic leukemia; Accession No. NM_001287347), LYL1 (lymphoblastic leukemia derived sequence 1; Accession No. NM_005583), LMO2 (LIM domain only 2 (rhombotin-like 1); Accession No. M_001142315), GATA2 (GATA binding protein 2; Accession No. NM_001145661), or GATA3 (GATA binding protein 3; Accession No. NM_001002295). In particular embodiments, the hematopoietic development gene is GATA2.

3. Homeobox Genes

In addition, the multi-lineage construct(s) encodes at least one homeobox gene. Homeobox genes encode a homeobox about 180 base pairs long that encodes a protein domain that binds DNA. The characteristic homeodomain protein fold consists of a 60-amino acid helix-turn-helix (HTH) structure in which three alpha helices are connected by short loop regions. The N-terminal two helices are antiparallel and the longer C-terminal helix is roughly perpendicular to the axes established by the first two. It is this third helix that interacts directly with DNA via a number of hydrogen bonds and hydrophobic interactions, which occur between specific side chains and the exposed bases and thymine methyl groups within the major groove of the DNA. Many homeodomain proteins induce cellular differentiation by initiating the cascades of coregulated genes required to produce individual tissues and organs.

The homeobox gene may be any gene encoding a homeobox domain. For example, the homeobox gene could be a HOX gene such as HOXA9 (Accession No. NM_152739), HOXA10 (Accession No. NM_018951), HOXA3 (Accession No. NM_030661), HOXA4 (Accession No. NM_002141), HOXA5 (Accession No. NM_019102), HOXA6 (Accession No. NM_024014), HOXA7 (Accession No. NM_006896), HOXB3 (Accession No. NM_002146), or HOXB6 (Accession No. NM_018952). Other non-limiting examples of HOX genes include Activity-dependent neuroprotector homeobox (ADNP; Accession No. NM_001282531), Homeobox protein aristaless-like 4 (ALX4; Accession No. NM_021926), Homeobox protein DBX1 (Accession No. NM_001029865), Double homeobox 4 (DUX4; NM_001127386), Homeobox protein EMX1 (Accession No. NM_001040404), GBX2 (Accession No. NM_001301687), Homeobox expressed in ES cells 1 (HESX1; Accession No. NM_003865), NANOG (Accession No. NM_001297698), PAX3 (Accession No. NM_000438), retina and anterior neural fold homeobox (RAX; Accession No. NM_013435), or Zinc finger E-box-binding homeobox 1 (ZEB1; Accession No. NM_001128128). In particular embodiments, the homeobox gene is HOXA9.

B. Hematopoietic Stem Cell Programming Factors

Certain aspects of the present disclosure provide constructs encoding hematopoietic stem cell programming factors for long-term engraftment potential. Hematopoietic stem cells capable of long-term engraftment could be produced directly from the multi-lineage hematopoietic precursor cells of the present disclosure by increasing the level of hematopoietic stem cell programming gene(s), particularly the genes listed in Table 1, in the cells. The inventors also contemplate that all isoforms and variants of the genes listed in this section are included in the present disclosure, and non-limiting examples of accession numbers for certain isoforms or variants are provided.

Table 1 provides a list of genes for programming multi-lineage hematopoietic precursors to hematopoietic stem cells capable of long-term engraftment. All of the gene sequence and related information provided by the listed Gene ID and Accession numbers is hereby incorporated by reference as of the filing date of this application.

TABLE 1

Hematopoietic stem cell programming genes for long-term engraftment potential.

| # | Symbol | Gene ID | Accession | Full name |
|---|---|---|---|---|
| 1 | BCL2 | 596 | NM_000633; NM_000657 | B-cell CLL/lymphoma 2 |
| 2 | BEND4 | 389206 | NM_207406; NM_001159547 | BEN domain containing 4 |
| 3 | BMI1 | 648 | NM_005180 | BMI1 polycomb ring finger oncogene |
| 4 | CIITA | 4261 | NM_001286402; NM_000246; NM_001286403 | class II, major histocompatibility complex, transactivator |
| 5 | EGR3 | 1960 | NM_004430; NM_001199880; NM_001199881 | early growth response 3 |
| 6 | ETV6 | 2120 | NM_001987 | Ets variant 6 |
| 7 | EZH1 | 2145 | NM_001991 | enhancer of zeste 1 polycomb repressive complex 2 subunit |
| 8 | EZH2 | 2146 | NM_001203247; NM_001203248; NM_001203249; NM_004456; NM_152998 | enhancer of zeste 2 polycomb repressive complex 2 subunit |
| 9 | FOXL1 | 2300 | NM_005250 | forkhead box L1 |
| 10 | HIF3A | 64344 | NM_152794; NM_022462; NM_152795; NM_152796 | hypoxia inducible factor 3, alpha subunit |
| 11 | HLF | 3131 | NM_002126 | Hepatic leukemia factor |
| 12 | HOXA10 | 3206 | NM_018951; NM_153715 | Homeobox A10 |
| 13 | HOXA3 | 3200 | NM_030661 | homeobox A3 |
| 14 | HOXA4 | 3201 | NM_002141 | Homeobox A4 |
| 15 | HOXA5 | 3202 | NM_019102 | Homeobox A5 |
| 16 | HOXA6 | 3203 | NM_024014 | Homeobox A6 |
| 17 | HOXA7 | 3204 | NM_006896 | Homeobox A7 |
| 18 | HOXA9 | 3205 | NM_152739 | Homeobox A9 |
| 19 | HOXB3 | 3213 | NM_002146 | homeobox B3 |
| 20 | HOXB6 | 3216 | NM_018952 | homeobox B6 |
| 21 | HSF5 | 124535 | NM_001080439 | heat shock transcription factor family member 5 |
| 22 | KLF2 | 10365 | NM_016270 | Kruppel-like factor 2 |
| 23 | KLF4 | 9314 | NM_004235 | Kruppel-like factor 4 (gut) |
| 24 | MECOM | 2122 | NM_001105077; NM_001105078; NM_001163999; NM_001164000; NM_004991 | MDS1 and EVI1 complex locus |
| 25 | MEIS1 | 4211 | NM_002398 | Meis homeobox 1 |
| 26 | MIR29A | 407021 | NR_029503 | microRNA 29a |
| 27 | MIR29B1 | 407024 | NR_029517 | microRNA 29b-1 |
| 28 | MSI2 | 124540 | NM_138962; NM_170721 | musashi RNA-binding protein 2 |
| 29 | MYB | 4602 | NM_001130172; NM_001130173; NM_001161656; NM_001161657; NM_001161658; NM_001161659; NM_001161660; NM_005375 | v-myb myeloblastosis viral oncogene homolog (avian) |
| 30 | MYCN | 4613 | NM_001293228; NM_001293233; NM_001293231 | v-myc avian myelocytomatosis viral oncogene neuroblastoma derived homolog |
| 31 | NA9 | | | NUP98-HOXA9 fusion protein |
| 32 | NA9HD | | | NUP98-HOXA9 homeodomain fusion protein |
| 33 | NA10 | | | NUP98-HOXA10 fusion protein |
| 34 | NA10HD | | | NUP98-HOXA10 homeodomain fusion protein |
| 35 | NKX2-3 | 159296 | NM_145285 | NK2 homeobox 3 |
| 36 | NR4A2 | 4929 | NM_006186 | nuclear receptor subfamily 4, group A, member 2 |
| 37 | PEG3 | 5178 | NM_006210; NM_001146185; NM_001146187 | paternally expressed 3 |
| 38 | PRDM12 | 59335 | NM_021619 | PR domain containing 12 |
| 39 | PRDM16 | 63976 | NM_022114; NM_199454 | PR domain containing 16 |
| 40 | RBAK | 57786 | NM_021163 | RB-associated KRAB zinc finger |
| 41 | RUNX1 (a) | 861 | NM_001122607 | Runt-related transcription factor 1 |
| 42 | RUNX3 | 864 | NM_001031680; NM_004350 | runt-related transcription factor 3 |
| 43 | SETBP1 | 26040 | NM_015559; NM_001130110 | SET binding protein 1 |
| 44 | SOX17 | 64321 | NM_022454 | SRY (sex determining region Y)-box 17 |
| 45 | SOX8 | 30812 | NM_014587 | SRY (sex determining region Y)-box 8 |
| 46 | TFEC | 22797 | NM_001018058; NM_001244583; NM_012252 | Transcription factor EC |
| 47 | ZBTB14 | 7541 | NM_001143823 | zinc finger and BTB domain containing 14 |
| 48 | ZBTB20 | 26137 | NM_001164342; NM_015642 | zinc finger and BTB domain containing 20 |

TABLE 1-continued

Hematopoietic stem cell programming genes for long-term engraftment potential.

| # | Symbol | Gene ID | Accession | Full name |
|---|--------|---------|-----------|-----------|
| 49 | ZMAT1 | 84460 | NM_001011657; NM_001282400 | zinc finger, matrin-type 1 |
| 50 | ZNF131 | 7690 | NM_001297548; NM_003432 | zinc finger protein 131 |
| 51 | ZNF134 | 7693 | NM_003435 | zinc finger protein 134 |
| 52 | ZNF136 | 7695 | NM_003437 | zinc finger protein 136 |
| 53 | ZNF256 | 10172 | NM_005773 | zinc finger protein 256 |
| 54 | ZNF26 | 7574 | NM_001256279; NM_019591; NM_001256280 | zinc finger protein 26 |
| 55 | ZNF300 | 91975 | NM_001172831; NM_001172832; NM_052860 | zinc finger protein 300 |
| 56 | ZNF337 | 26152 | NM_001290261 | zinc finger protein 337 |
| 57 | ZNF350 | 59348 | NM_021632 | zinc finger protein 350 |
| 58 | ZNF414 | 84330 | NM_001146175; NM_032370 | zinc finger protein 414 |
| 59 | ZNF662 | 389114 | NM_207404; NM_001134656 | zinc finger protein 662 |
| 60 | ZNF667 | 63934 | NM_022103 | zinc finger protein 667 |
| 61 | ZNF682 | 91120 | NM_033196; NM_001077349 | zinc finger protein 682 |
| 62 | HMGA2 | 8091 | NM_003483; NM_003484 NM_001330190; NM_001300919; NM_001300918 | high mobility group AT-hook 2 |

In some embodiments, a hematopoietic stem cell programming gene is any one of the genes included in Table 1, which includes genes involved in the specification of hematopoietic cells, genes involved in the maintenance and/or proliferation of hematopoietic cells, and genes expressed in hematopoietic cells.

In certain embodiments, one or more hematopoietic stem cell programming genes are used in combination for programming to hematopoietic stem cells capable of long-term engraftment. In some embodiments, three or more, such as 4, 5, 6, 7, 8, 9, 10, 15, up to 20 or any range derivable therein, hematopoietic stem cell programming genes are used in combination for programming to hematopoietic stem cells capable of long-term engraftment.

The hematopoietic stem cell programming gene can be fused to a sequence known in the art for expansion of the hematopoietic precursor cells (U.S. Patent Publication No. US20080299095, incorporated herein by reference). An exemplary sequence is NUP98 or a homeodomain thereof.

IV. DELIVERY OF HEMATOPOIETIC PROGRAMMING GENES

In certain embodiments, vectors for delivery of nucleic acids encoding programming factors are constructed to express those factors in the pluripotent stem cells. Details of the components of such vectors and delivery methods are disclosed below.

In a further aspect, the following systems and methods may also be used in delivery of a reporter expression cassette for identification of desired cell types, such as hematopoietic precursor cells. In particular, a regulatory element specific for hematopoietic stem cells or hematopoietic precursors may be used to drive expression of a reporter gene. Therefore hematopoietic stem cells or precursors derived from programming may be characterized, selected, or enriched via use of the reporter.

A. Nucleic Acid Delivery Systems

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

1. Viral Vectors

Viral vectors may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present disclosure are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

2. Episomal Vectors

The use of plasmid—or liposome-based extra-chromosomal (i.e., episomal) vectors may be also provided in certain aspects of the present disclosure. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-base vectors are also contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-based System

In certain aspects, the delivery of programming factors can use a transposon-transposase system. For example, the transposon-transposase system could be the well-known Sleeping Beauty, the Frog Prince transposon-transposase system (for a description of the latter, see, e.g., EP1507865), or the TTAA-specific transposon PiggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

In particular embodiments, the constructs (e.g., the multi-lineage construct) provided in the present disclosure use a PiggyBac expression system. PiggyBac (PB) DNA transposons mobilize via a "cut-and-paste" mechanism whereby a transposase enzyme (PB transposase), encoded by the transposon itself, excises and re-integrates the transposon at other sites within the genome. PB transposase specifically recognizes PB inverted terminal repeats (ITRs) that flank the transposon; it binds to these sequences and catalyzes excision of the transposon. PB then integrates at TTAA sites throughout the genome, in a relatively random fashion. For the creation of gene trap mutations (or adapted for generating transgenic animals), the transposase is supplied in trans on one plasmid and is co-transfected with a plasmid containing donor transposon, a recombinant transposon comprising a gene trap flanked by the binding sites for the transposase (ITRs). The transposase will catalyze the excision of the transposon from the plasmid and subsequent integration into the genome. Integration within a coding region will capture the elements necessary for gene trap expression. PB possesses several ideal properties: (1) it preferentially inserts within genes (50 to 67% of insertions hit genes) (2) it exhibits no local hopping (widespread genomic coverage) (3) it is not sensitive to over-production inhibition in which elevated levels of the transposase cause decreased transposition 4) it excises cleanly from a donor site, leaving no "footprint," unlike Sleeping Beauty.

4. Homologous Recombination

In certain aspects, nucleic acid molecules can be introduced into cells in a specific manner for genome engineering, for example, via homologous recombination. As discussed above, some approaches to express genes in cells involve the use of viral vectors or transgenes that integrate randomly in the genome. These approaches, however, have the drawback of integration occurring either at sites that are unable to effectively mediate expression from the integrated nucleic or that result in the disruption of native genes. Problems associated with random integration could be partially overcome by homologous recombination to a specific locus in the target genome, e.g., Rosa26 locus.

Homologous recombination (HR), also known as general recombination, is a type of genetic recombination used in all forms of life in which nucleotide sequences are exchanged between two similar or identical strands of DNA. The technique has been the standard method for genome engineering in mammalian cells since the mid-1980s. The process involves several steps of physical breaking and the eventual rejoining of DNA. This process is most widely used to repair potentially lethal double-strand breaks in DNA. In addition, homologous recombination produces new combinations of DNA sequences during meiosis, the process by which eukaryotes make germ cells like sperm and ova. These new combinations of DNA represent genetic variation in offspring which allow populations to evolutionarily adapt to changing environmental conditions over time. Homologous recombination is also used in horizontal gene transfer to exchange genetic material between different strains and species of bacteria and viruses. Homologous recombination is also used as a technique in molecular biology for introducing genetic changes into target organisms.

Homologous recombination can be used as targeted genome modification. The efficiency of standard HR in mammalian cells is only 10-6 to 10-9 of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002).

On the path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005).

Another class of such specificity molecules includes Transcription Activator Like Effector (TALE) DNA binding domains fused to the catalytic domain of a Type IIS restriction endonuclease such as FokI (Miller et al., 2011; PCT/1B2010/000154). TALENs can be designed for site-specific genome modification at virtually any given site of interest (Cermak et al., 2011; Christian et al., 2010; Li et al., 2011; Miller et al., 2011; Weber et al., 2011; Zhang et al., 2011). The site-specific DNA binding domain is expressed as a fusion protein with a DNA cleavage enzyme such as Fok I. The DNA binding domain is a scaffold of repeating amino acids; linking each of the repeats are two variable amino acids that bind to a single nucleotide in the DNA. For example, Asn-Asn binds guanosine, Asn-Ile binds adenosine, Asn-Gly bind thymidine, and His-Asp binds Cytosine. These two amino acids are known as the Repeat Variable Diresidue or RVD. There are many different RVD's and they can be engineered into the TAL Effector/Fok1 protein construct to create a specific TALEN. The RNA encoding the recombinant TALEN can then be purified and transfected into a cell for site-specific genome modification. Once the TALEN introduces the double strand DNA break, the DNA can be modified by non-homologous end joining (NHEJ) or by homologous directed repair (HDR). This allows DNA mutagenesis, deletions, or additions depending on what additional sequences are present during the DNA repair.

B. Regulatory Elements

Expression cassettes included in vectors useful in the present disclosure preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

The expression constructs provided herein comprise promoter to drive expression of the programming genes. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

Tissue-specific transgene expression, especially for reporter gene expression in hematopoietic cells and precursors of hematopoietic cells derived from programming, may be desirable as a way to identify derived hematopoietic cells and precursors. To increase both specificity and activity, the use of cis-acting regulatory elements has been contemplated. For example, a hematopoietic cell-specific promoter may be used. Many such hematopoietic cell-specific promoters are known in the art, such as promoters of the hematopoietic genes provided in Table 1.

In certain aspects, the present methods also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many hematopoietic cell promoter and enhancer sequences have been identified, and may be useful in present methods. See, e.g., U.S. Pat. No. 5,556,954; U.S. Patent App. 20020055144; U.S. Patent App. 20090148425.

In particular aspects, the promoter is an inducible promoter. The activity of inducible promoters may be induced by the presence or absence of biotic or abiotic factors. Inducible promoters are a very powerful tool in genetic engineering because the expression of genes operably linked to them can be turned on or off at certain stages of development of an organism or in a particular tissue. For example, Tet-On and Tet-Off inducible gene expression systems based on the essential regulatory components of the E. coli tetracycline-resistance operon may be used. Once established in the starting cells, the inducer doxycycline (Dox, a tetracycline derivative) could control the expression system in a dose-dependent manner, allowing the precise modulation of the expression levels of programming genes. In exemplary embodiments, the inducible promoter is an rtTET-inducible Tight promoter (pTight). Thus, the pTight promoter could be used to induce expression of the multi-lineage programming genes such as ETV2, GATA2 and HOXA9 for a period of time sufficient to allow programming of the PSCs to hematopoietic precursor cells, and the expression could subsequently be turned off. The pTight promoter could also be a bi-directional promoter.

2. Initiation Signals and Linked Expression

A specific initiation signal also may be used in the expression constructs provided in the present methods for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of programming genes in the constructs provided in the present disclosure. For example, cleavage sequences could be used to co-express genes by linking open reading frames to form a single cistron. An exemplary cleavage sequence is the F2A (Foot-and-mouth diease virus 2A) or a "2A-like" sequence (e.g., Thosea asigna virus 2A; T2A) (Minskaia and Ryan, 2013).

In particular embodiments, an F2A-cleavage peptide is used to link expression of the genes in the multi-lineage construct.

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In certain embodiments, cells containing a nucleic acid construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

C. Nucleic Acid Delivery

Introduction of a nucleic acid, such as DNA or RNA, into the pluripotent stem cells to be programmed to hematopoietic precursor cells with the present methods may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et at., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment, a nucleic acid may be introduced to the pluripotent stem cell by liposome-mediated transfection. In this method, the nucleic acid is entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary based upon the nature of the liposome as well as the cell used, for example, about 5 to about 20 μg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments, a liposome may be complexed with a hemagglutinating virus (HVJ). This has been shown to facilitate fusion with the cell membrane and promote cell entry of liposome-encapsulated DNA (Kaneda et cll., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 μg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

V. METHODS FOR PRODUCING HEMATOPOIETIC PRECURSOR CELLS

A. Multi-Lineage Hematopoietic Precursor Cells

The present disclosure provides methods for producing multi-lineage hematopoietic precursor cells from pluripotent stem cells (PSCs). PSCs, such as ESCs or iPSCs, are genetically modified to express the hematopoietic precursor programming genes described herein which forward program the PSCs into multi-lineage hematopoietic precursor cells. In particular, the multi-lineage hematopoietic precursors have the potential to differentiate into myeloid and lymphoid lineage cells. Preferably, the hematopoietic precursor programming genes comprise an ETS gene, a hematopoietic development gene and a homeobox gene. Exemplary hematopoietic precursor programming genes include EVT2 or ERG, GATA2 and HOXA9.

Additional hematopoietic precursor programming genes, such as HOXA10, can enhance the forward programming efficiency. In some aspects, the hematopoietic programming gene is fused to a sequence known in the art for expansion of the hematopoietic precursor cells (U.S. Patent Publication No. US20080299095, incorporated herein by reference). An exemplary sequence is NUP98 or a homeodomain thereof. In one exemplary method, the hematopoietic precursor programming genes include EVT2 or ERG, GATA2, HOXA9, NUP98-HOXA9 and NUP98-HOXA10.

The hematopoietic precursor programming genes can be encoded by one or more expression constructs. Preferably, the genes are encoded by one expression construct. Accordingly, the expression of the hematopoietic precursor programming genes can be under the control of a single promoter. The expression of the hematopoietic programming genes can be operably linked such as by IRES or 2A sequence elements.

Preferably, the three hematopoietic precursor programming genes are expressed for only a period of time sufficient to forward program the PSCs into hematopoietic precursor cells. Accordingly, the hematopoietic precursor programming genes can be under the control of an inducible promoter. Thus, the expression of the hematopoietic precursor programming genes can be induced in the PSCs for a period of time sufficient to forward program to the multi-lineage hematopoietic precursor cells. The period of time can be about 1 day to about 20 days, such as about 3, 4, 5, 6, 7, 8, 9, or 10 days. Alternatively, the hematopoietic precursor programming genes can be introduced to the PSCs by an episomal vector. Thus, the hematopoietic precursor programming genes could be transiently expressed in the PSCs.

The multi-lineage hematopoietic precursor cells can then be cultured further to produce lymphoid and myeloid lineage cells as well as be programmed further to engraftable hematopoietic stem cells.

B. Hematopoietic Cells for Long-Term Engraftment

The multi-lineage hematopoietic precursor cells can be further programmed to hematopoietic stem cells capable of long-term engraftment. Preferably, the PSCs or hematopoietic precursor cells are transfected with one or more additional expression construct(s) that encode one or more hematopoietic stem cell programming gene(s) described herein (e.g., Table 1) whose expression enables the multi-lineage hematopoietic precursors to be stably engrafted in vivo. The one or more additional expression constructs can be introduced to the PSCs concurrently with the multi-lineage construct(s) or after the PSCs have been forward programmed to the immature hematopoietic precursor cells.

The hematopoietic stem cell programming gene(s) for long-term engraftment can be encoded by one or more expression constructs. Preferably, multiple genes are encoded by an expression construct. Accordingly, the expression of the one or more hematopoietic stem cell programming gene(s) (i.e., long-term engraftment genes) can be under the control of a single promoter. The expression of the long-term engraftment genes can be operably linked such as by IRES or 2A sequence elements.

In certain aspects, the hematopoietic stem cell programming gene(s) for long-term engraftment are expressed in the multi-lineage hematopoietic precursors and not expressed in the PSCs. Accordingly, the hematopoietic stem cell programming gene(s) can be under the control of a promoter that is essentially silenced in PSCs. In one exemplary method, the hematopoietic stem cell programming gene is under the control of the cytomegalovirus (CMV) promoter. Alternatively, the hematopoietic stem cell programming gene(s) can be under the control of an inducible promoter. Thus, expression of the hematopoietic stem cell programming gene(s) can be induced after the PSCs have been forward programmed to the multi-lineage hematopoietic precursor cells. In yet another alternative, the construct(s) encoding the hematopoietic stem cell programming gene(s) can be transfected into the immature hematopoietic precursor cells after they have been forward programmed from PSCs.

C. Cell Culture

The multi-lineage hematopoietic precursor cells or the hematopoietic stem cells capable of long-term engraftment can be cultured under conditions for hematopoietic stem cell culture known in the art. In particular, the hematopoietic precursor cells can also be cultured under conditions to derive specific hematopoietic lineages such as myeloid or lymphoid lineages.

Generally, cells of the present disclosure are cultured in a culture medium, which is a nutrient-rich buffered solution capable of sustaining cell growth. Culture media suitable for isolating, expanding and differentiating pluripotent stem cells into hematopoietic precursor cells and hematopoietic cells according to the method described herein include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non-essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 8/464,599 and WO96/39487, and the "complete media" as described in U.S. Pat. No. 5,486,359 are contemplated for use with methods described herein. In some embodiments, the culture medium is supplemented with 10% Fetal Bovine Serum (FBS), human autologous serum, human AB serum or platelet rich plasma supplemented with heparin (2 U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

Pluripotent stem cells to be differentiated into hematopoietic cells and their precursors may be cultured in a medium sufficient to maintain the pluripotency. Culturing of induced pluripotent stem cells generated in certain aspects of the present disclosure can use various media and techniques developed to culture primate pluripotent stem cells, more specially, embryonic stem cells, as described in U.S. Pat. App. 20070238170 and U.S. Pat. App. 20030211603. For example, like human embryonic stem cells, induced pluripotent stem cells can be maintained in 80% DMEM/F12 (Gibco #11330032 or #11320082), 20% KnockOut serum replacement, 1% non-essential amino acids, 1 mM L-glutamine, 0.1 mM β-mercaptoethanol, and bFGF (4-100 ng/mL) (PCT Appln. WO 99/20741). Alternatively, human ES cells and iPS cells can be maintained in chemically defined serum-free medium, such as mTeSR1.

Hematopoietic cells and their precursors can be generated by culturing pluripotent stem cells or other non-hematopoietic cells in a medium under conditions that increase the intracellular level of hematopoietic programming factors to be sufficient to promote programming of the cells into hematopoietic precursor cells. The medium may also contain one or more hematopoietic cell differentiation and maturation agents, like various kinds of growth factors. These agents may either help induce cells to commit to a more mature phenotype—or preferentially promote survival of the mature cells—or have a combination of both of these effects. Hematopoietic precursor cell and hematopoietic cell differentiation and maturation agents may include soluble growth factors (peptide hormones, cytokines, ligand-receptor complexes, and other compounds) that are capable of promoting the growth of cells of the hematopoietic cell lineage. Non-limiting examples of such agents include but are not limited to hematopoietic or endothelial growth factors such as fibroblast growth factor (FGF), vascular endothelial growth factor (VEGF), stem cell factor (SCF), thrombopoietin (TPO), FLT-3 ligand (FLT3L), interleukin-3 (IL-3), interleukin-6 (IL-6), interleukin-9 (IL-9), or granulocyte colony-stimulating factor (G-CSF), or isoforms or variants thereof.

VI. HEMATOPOIETIC PRECUSOR CELL AND HEMATOPOIETIC STEM CELL CHARACTERSTICS

The hematopoietic precursor cells and the hematopoietic stem cells of the present disclosure can be characterized according to a number of phenotypic criteria. The criteria include but are not limited to the detection or quantitation of expressed cell markers, functional activity, and the characterization of morphological features and intercellular signaling. In other aspects, cells to be programmed may comprise a reporter gene expression cassette comprising tissue- or cell-specific transcriptional regulatory elements, like hematopoietic cell-specific promoters for hematopoietic cell identification.

Hematopoietic precursor cells embodied in certain aspects of the present disclosure have morphological features characteristic of hematopoietic precursor cells in nature. The features are readily appreciated by those skilled in evaluating such things, and include the detection of cell clusters producing round non-adherent cells. In addition, hematopoietic precursor cells have a rounded shape and a low cytoplasm-to-nucleus ratio.

Cells of the present disclosure can also be characterized according to whether they express certain markers characteristic of cells of the hematopoietic cell lineage. Non-limiting examples of cell markers useful in distinguishing hematopoietic stem cells and precursors of hematopoietic cells include: CD43, CD33, CD34, CD45, CD235a, CD38, CD90, CD133, CD105, CD117 (c-kit; the receptor for SCF), CD74, and CD41a. For example, immature hematopoietic precursors capable of differentiating to myeloid and lymphoid lineages could be distinguished by being positive for CD43 and CD34. To identify cells that have differentiated from multi-potent starting cells, such as ESCs or iPSCs, it may be useful to identify cells that do not express certain markers that are present on pluripotent stem cells or somatic cells, such as TRA-1-60, TRA-1-81, CD166, or CD140b.

Assessment of the level of expression of such markers can be determined in comparison with other cells. Positive controls for the markers of hematopoietic precursor cells or hematopoietic cells include adult hematopoietic cells or hematopoietic stem cells of the species of interest, and established hematopoietic cell lines. The reader is cautioned that permanent cell lines or long-term hematopoietic cells cultures may be metabolically altered, and fail to express certain characteristics of primary hematopoietic cells and hematopoietic precursor cells. Negative controls include cells of a separate lineage, such as an adult fibroblast cell line, adult mesenchymal stem cells, or retinal pigment epithelial (RPE) cells. Undifferentiated stem cells are positive for some of the markers listed above, but negative for certain markers of hematopoietic cells and hematopoietic precursor cells, as illustrated in the examples below.

Hematopoietic-specific protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of specific (e.g., hematopoietic precursor cell-specific) markers can also be detected at the mRNA level by Northern blot analysis, dot-blot hybridization analysis, or by reverse-transcription polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display a functional activity that is characteristic of cells of the hematopoietic lineage. For example, hematopoietic precursor cells have the ability to self-renew and can give rise to more than one type of hematopoietic cell. In particular embodiments, the hematopoietic precursor cells obtained can efficiently give rise to lymphoid cells (such as, for example, T cells, B cells, and NK cells), erythro-megakaryocytic cells (such as, for example, erythrocytes and thrombocytes), and myeloid cells (such as, for example, granulocytes and monocytes) in vitro. In other embodiments, the hematopoietic stem cells are capable of long-term engraftment in mammals. For example, long-term engraftment in a mouse model could be characterized by the presence of human hematopoietic cells (e.g., cells that are $CD45^+$ and HLA Class I+) in the peripheral blood and/or bone marrow such as at 6, 12, 18, 20, or 25 weeks after engraftment.

Hematopoietic precursor cells and hematopoietic stem cells provided by programming according to the present methods can have a number of the features of the stage of cell they are intended to represent. The more of these features that are present in a particular cell, the more it can be characterized as a cell of the hematopoietic cell lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

VII. USES OF HEMATOPOIETIC PRECURSOR CELLS AND HEMATOPOIETIC STEM CELLS

The hematopoietic precursor cells and hematopoietic stem cells provided by methods and compositions of certain aspects of the present disclosure can be used in a variety of applications. These include but are not limited to transplantation or implantation of the hematopoietic cells and hematopoietic precursor in vivo; screening cytotoxic compounds, carcinogens, mutagens growth/regulatory factors, pharmaceutical compounds, etc., in vitro; elucidating the mechanism of hematological diseases and injuries; studying the mechanism by which drugs and/or growth factors operate; diagnosing and monitoring cancer in a patient; gene therapy; and the production of biologically active products, to name but a few.

A. Test Compound Screening

Programming-derived hematopoietic precursor cells and hematopoietic stem cells of the present disclosure can be used to screen for factors (such as solvents, small molecule drugs, peptides, and polynucleotides) or environmental conditions (such as culture conditions or manipulation) that affect the characteristics of hematopoietic cells provided herein.

Particular screening applications of the present disclosure relate to the testing of pharmaceutical compounds in drug research. The reader is referred generally to the standard textbook In vitro *Methods in Pharmaceutical Research*, Academic Press, 1997, and U.S. Pat. No. 5,030,015). In certain aspects, cells programmed to the hematopoietic lineage play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

In some applications, compounds may be screened for toxicity to hematopoietic stem cells or hematopoietic precursor cells.

B. Hematopoietic Cell Therapy

This present disclosure also provides for the use of hematopoietic stem cells and hematopoietic precursor cells provided herein to restore a degree of function to a subject needing such therapy, perhaps due to a hematological disease or disorder or an injury. For example, hematopoietic cells and hematopoietic precursor cells derived by methods disclosed herein may be used to treat hematological diseases and disorders such as hemoglobinopathies, anemias, etc. In addition, hematopoietic stem cells and their precursors may be useful in supplying blood or blood cells (such as, for example, red blood cells, platelets, and neutrophil granulocytes) to subjects in need thereof (such as, for example, subjects in need of a blood transfusion or subjects having a hematological disorder). Such cells may be useful for the treatment of hematopoietic cell deficiencies caused by cell-suppressive therapies, such as chemotherapy.

To determine the suitability of hematopoietic stem cells and precursors provided herein for therapeutic applications, the cells can first be tested in a suitable animal model. At one level, cells are assessed for their ability to survive and maintain their phenotype in vivo. Programmed cells provided herein are administered to immunodeficient animals (such as NOG mice, or animals rendered immunodeficient chemically or by irradiation) at a site amenable for further observation, such as under the kidney capsule, into the spleen, into a liver lobule, or into the bone marrow. Tissues are harvested after a period of a few days to several weeks or more, and assessed as to whether starting cell types such as pluripotent stem cells are still present. This can be performed by providing the administered cells with a detectable label (such as green fluorescent protein, or (3-galactosidase); or by measuring a constitutive marker specific for the administered human cells. Where programmed cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Hematopoietic stem cells and hematopoietic precursors provided by methods of the present disclosure may be tested in various animal models for their ability to treat hematological disorders and injuries. For example, a sickle cell anemia mouse model or the TB cell-deficient Rag-2 knock-out mouse may be particularly useful animal models for testing the hematopoietic cells and hematopoietic precursors disclosed herein.

Hematopoietic stem cells and hematopoietic precursor cells provided in certain aspects of the present disclosure that demonstrate desirable functional characteristics or efficacy in animal models, may also be suitable for direct administration to human subjects in need thereof. For purposes of hemostasis, the cells can be administered at any site that has adequate access to the circulation. Hematopoietic cells or precursors thereof may also be delivered at a site of injury or disease.

The cells provided herein can be used for therapy of any subject in need thereof. Human conditions that may be appropriate for such therapy include the various anemias and hemoglobinopathies, as well as diseases characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Distribution for Commercial, Therapeutic, and Research Purposes

For purposes of manufacture, distribution, and use, the hematopoietic precursor cells and hematopoietic stem cells of the present disclosure are typically supplied in the form of a cell culture or suspension in an isotonic excipient or culture medium, optionally frozen to facilitate transportation or storage.

The present disclosure also includes different reagent systems, comprising a set or combination of cells that exist at any time during manufacture, distribution, or use. The cell sets comprise any combination of two or more cell populations described in this disclosure, exemplified but not limited to programming-derived cells (hematopoietic lineage cells, their precursors and subtypes), in combination with undifferentiated stem cells, somatic cell-derived hematopoietic cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Linked Expression of ETV2/ERG, GATA2 and HOXA9 Efficiently Programs Human PSCs to Immature CD34+ Hematopoietic Progenitors The present studies were conducted to produce hematopoietic precursors with multi-lineage potential including myeloid and lymphoid potential. Multiple configurations of programming genes were tested for programming efficiency to achieve multi-lineage potential (Table 2). Coding regions of the transgenes were cloned into PiggyBac expression vectors under the control of the rtTET-inducible Tight promoter (pTight). ETV2/ERG and GATA2 (E+G) were cloned in separate expression vectors bearing blasticidin and geneticin resistance, respectively. Combined blasticidin and geneticin selection was used to achieve ETV2/ERG and GATA2 co-expression in transfected cells. Alternatively, for balanced uniform expression in transfected cells, ETV2/ERG and GATA2 (EG) were linked through the F2A-cleaveage peptide in one pTight-controlled expression cassette. It was found that the linked co-expression of ETV2/ERG and GATA2 (EG) resulted in significantly improved programming efficiency, and appeared to bypass the intermediate endothelial cell stage that was seen when ETV2/ERG and GATA2 (E+G) were expressed on separate vectors (FIG. 1).

TABLE 2

| Configurations of programming genes | |
|---|---|
| E + G | ETV2/ERG and GATA2 in separate vectors |
| EG | ETV2/ERG and GATA2 co-expressed in a single vector |
| EGH | ETV2/ERG, GATA2 and HOXA9 co-expressed in a single vector |

Next, HOXA9 was linked to the EG expression cassette (EGH) using a bi-directional Tight promoter (bi-pTight) to determine if HOXA9 can improve programming efficiency to produce hematopoietic precursors with multi-lineage potential including myeloid and lymphoid potential. E+G, EG and EGH inductive gene configurations were tested using human PSCs engineered to constitutively express rtTET protein for the doxycycline (DOX)-inducible gene expression. PiggyBac transgene vectors were introduced along with the hPBase-expressing vector into the rtTET-expressing human PSCs using electroporation. Cells with stable PiggyBac transposon integration were selected in culture with 100 µg/ml of blasticidin and/or geneticin. For transgene-induced hematopoietic programming, transfected PSCs were dissociated using 0.5 mM EDTA for about 5-10 minutes, resuspended in PSC culture medium (e.g., TeSR or E8®), and plated on matrigel-coated 6-well plates at $5\text{-}10 \times 10^4$ cells/well in PSC culture medium supplemented with 5 µM of the ROCK inhibitor blebbistatin. On the next day, transgene expression and hematopoietic induction was initiated by replacing PSC culture medium with 3 ml/well of Induction Medium (Table 3) supplemented with 0.25 µg/ml of doxycycline. Induction medium was changed every second day and cultures were harvested on day 8 of induction using Accutase (Innovative Cell Technologies) cell dissociation solution.

TABLE 3

| Induction Medium | |
|---|---|
| Component | Concentration |
| Iscove's Modified Dulbecco's Medium (IMDM) | |
| Polyvinyl-Alcohol | 100 µg/ml |
| Recombinant Human Albumin | 100 µg/ml |
| Human Transferrin | 20 µg/ml |
| Chemically-Defined Lipid Concentrate | 1/1000; Gibco |
| Linoleic Acid | 0.3 µM |
| Ascorbic Acid Magnesium Phosphate | 150 µM |
| N-Acetyl Cysteine | 100 µM |
| Trace Elements Supplements A | 1/5000 |

TABLE 3-continued

Induction Medium

| Component | Concentration |
| --- | --- |
| Trace Elements Supplements B | 1/2000 |
| Trace Elements Supplements C | 1/4000; Corning |
| Sodium Chloride | 5 mM |
| Heparin | 0.1 µg/ml |
| Putrescine | 0.5 µM |
| Ethanolamine | 20 µM |
| Monothioglycerol | 100 µM |
| Insulin | 100 ng/ml |
| IGF1 | 100 ng/ml |
| FGF2 | 2 ng/ml |
| SCF | 100 ng/ml |
| TPO | 10 ng/ml |

Figure 1B:
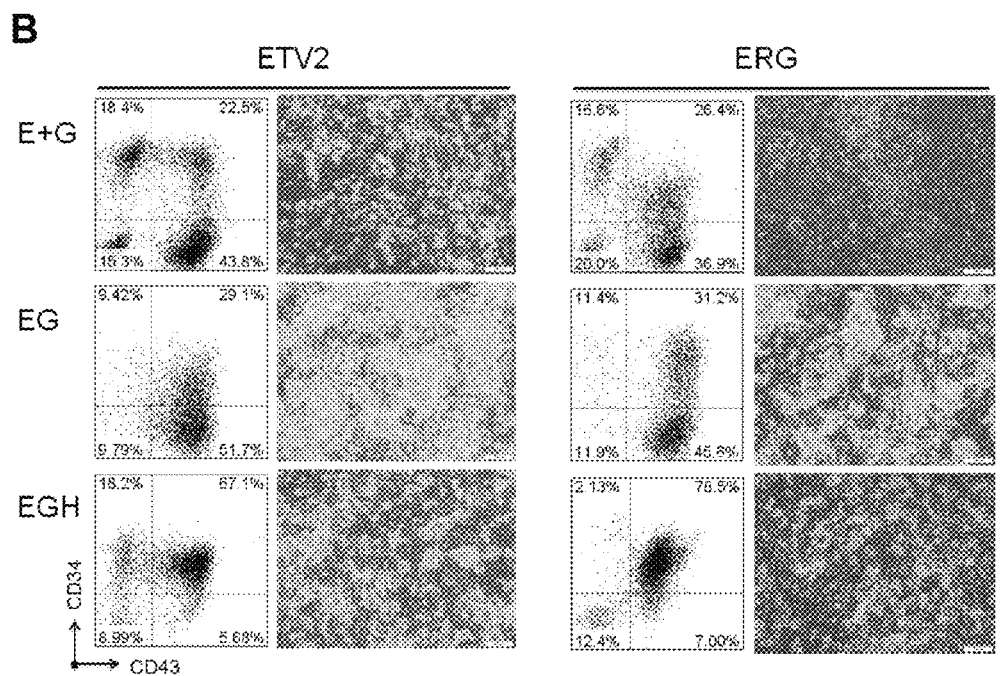
Figure 1C:
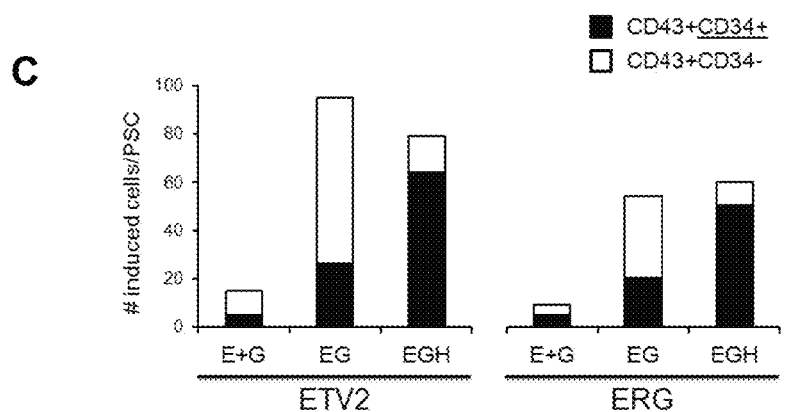
Figure 1D:

Harvested cells were counted and analyzed by flow cytometry for measurement of $CD34^+CD43^-$ endothelial cells, $CD43^+$ total hematopoietic cells and $CD43^+CD34^+$ immature hematopoietic progenitors. Dot-plots and images demonstrated that in both ETV2- and ERG-based gene configurations, induction with separate E+G genes resulted in the mixed $CD34^-CD43^-$ endothelial and $CD43^+$ hematopoietic populations, while linked EG genes efficiently (>80%) programmed human PSCs to $CD43^+$ hematopoietic population. More importantly, while proportions of immature $CD43^+CD34^+$ progenitors were similar in E+G and EG-induced cultures (30-40% of total $CD43^+$ cells) suggesting a similar differentiation rate in hematopoietic cells, the ETV2/ERG-GAT2-HOXA9 (EGH) gene configuration efficiently induced and maintained the immature population of hematopoietic progenitors as shown by $CD34^+$ expression in more than 90% of the $CD43^+$ cells (FIG. 1B). Absolute cell counts in 8 day DOX-induced cultures demonstrated that in both ETV2- and ERG-based gene configurations, the total number of the induced $CD43^-$ hematopoietic cells was significantly (e.g., more than 5-fold) increased through the linkage of inductive genes (EG), while more than a 2-fold higher number of immature $CD34^+CD43^+$ progenitors was specifically induced by the HOXA9-containing EGH gene configuration (FIG. 1C).

Figure 1E:
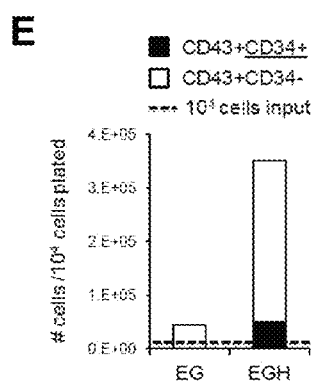
Figure 1F:
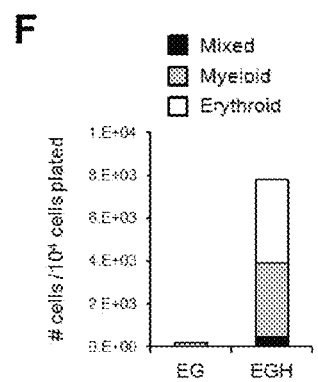

To examine the functional characteristics of EG- and EGH-induced hematopoietic cells, expansion and differentiation potentials of 8 day DOX-induced cells were tested in co-culture with MS5 stromal cells. Induced cells were plated at $10^4$ cells/well into 6-well plates with mitomycin C-treated MS5 cell monolayers in 4 ml/well Co-culture Medium (Table 4). Cultures were maintained for 2 weeks with a half medium change every 3 days. Non-adherent cells were collected and cell monolayers were dissociated by successive treatments with 1 mg/ml collagenase IV for 15 minutes and Accutase for 15 minutes. Non-adherent and dissociated adherent cell fractions were combined and used for analysis of absolute cell counts, proportions of total $CD43^+$ and immature $CD34^+CD43^+$ hematopoietic cells by flow cytometry, and colony-forming cells by the MethoCult assay (StemCell Technologies). In contrast to EG-induced cells, which showed very limited growth mostly attributed to small floating cell clusters, EGH-induced cells demonstrated robust expansion with remarkable and extensive cobblestone-like growth areas (FIG. 1D), a well-known feature of very primitive hematopoietic progenitors. Absolute counts of total CD43+ and immature $CD43+CD34^+$ cells demonstrated only about a 5-fold increase of total $CD43^+$ cells and a lack of immature $CD34^+CD43^+$+ cells in the expanded EG-induced cells. In contrast, the total $CD43^+$ hematopoietic cells expanded by more than 30-fold, and $CD43^+CD34^+$ immature cells expanded by about 5-fold in the EGH-induced cells (FIG. 1E). While the colony-forming potential was severely depleted in EG-induced cells with only a few myeloid colonies detected, multi-lineage colony-forming potential was detected in EGH-induced cells following a 2 week co-culture with MS5 stroma (FIG. 1F).

TABLE 4

Co-culture Medium

| Component | Concentration |
| --- | --- |
| Iscove's Modified Dulbecco's Medium (IMDM) | |
| FBS (HyClone) | 10% |
| Glutamax (Gibco) | 1:100 |
| Monothioglycerol | 100 µM |
| FGF1 | 2 ng/mL |
| IGF1 | 50 ng/mL |
| SCF | 100 ng/mL |
| FLT3L | 100 ng/mL |
| TPO | 10 ng/mL |
| IL3 (only added at cell plating) | 10 ng/mL |

Example 2

Enhancement of the Multi-Lineage Potential of Immature Hematopoietic Precursors Additional genes were screened to improve the forward programming efficiency of PSCs to the immature hematopoietic progenitors. A screening model was devised to detect additional genes that could be complementary to ETV2/ERG-GATA2-HOXA9 (EGH) for improved production of immature, $CD43^+CD34^-$ and $CD43^-CD34^-CD133^+$ cells.

Figure 2:
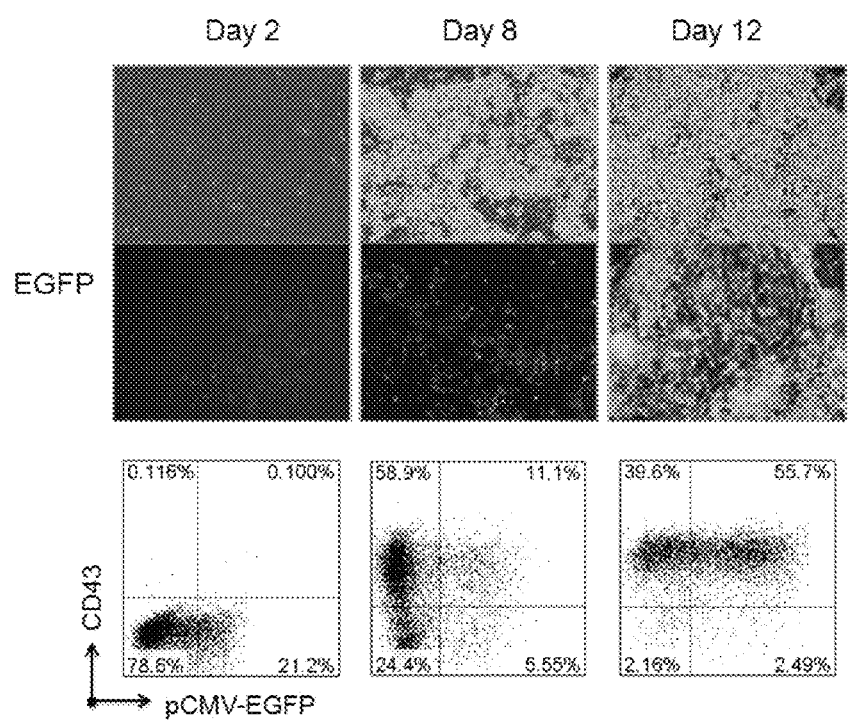
FIG. 2: Post-induction transgene expression using the CMV promoter (pCMV). pCMV-EGFP and pTight-EG constructs were introduced into rtTET-expressing human PSCs using PiggyBac expression vectors. EGFP expression in $CD43^+$ cells is shown following DOX-induced hematopoietic programming.

Since pCMV has been shown to be essentially suppressed in undifferentiated human PSCs and to have active expression in differentiated cells such as HPCs, studies were conducted to find out whether this feature of the CMV promoter could be used for post-induction gene expression in the induced $CD43^+$ cells. pCMV-EGFP and pTight-EG constructs were introduced in rtTET-expressing human PSCs using PiggyBac expression vectors. EGFP expression in $CD43^+$ cells was monitored following DOX-induced hematopoietic programming. In the undifferentiated/non-induced iPSCs, and up to day 8 of DOX-induction, low EGFP expression was detected in about 20% of the cells, including the induced $CD43^+$ cells. In contrast, after an additional 4 days (e.g., Day 12), high EGFP expression was detected in more than 50% of the induced $CD43^+$ cells (FIG. 2). Thus, the pCMV promoter could be used for post-induction transgene expression of the additional genes.

Figure 3A:
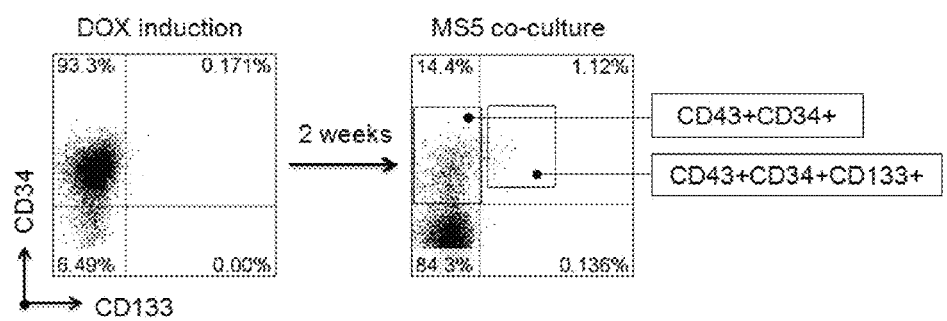
FIGS. 3A-3C: Screening for EGH-complementary transgenes that improve the expansion and confer CD133 expression of primitive hematopoietic progenitors. (A) EGH-induced cells with constitutive HOXA10 expression (pCMV) show a minor population of $CD43^+CD34^+CD133^+$ cells associated with the most primitive stem cell-like cells following a 2 week co-culture with MS5 stroma. (B) Schematic of the screening model devised to detect EGH-complementary genes for improved primitive $CD43^+CD34^+$ and $CD43^+CD34^+CD133^+$ cell production. (C) Screening results for genes demonstrating positive effect on the expansion of EGH-induced primitive progenitors are shown. Score=P34×P133×(P34/P45), where P—production of respective subset calculated as a fraction of internal EGH control, 34—$CD43^+CD34^+$, 133—$CD43^+CD34^+CD133^+$, 45—$CD43/45^+CD34^-$ cells.
Figure 3B:
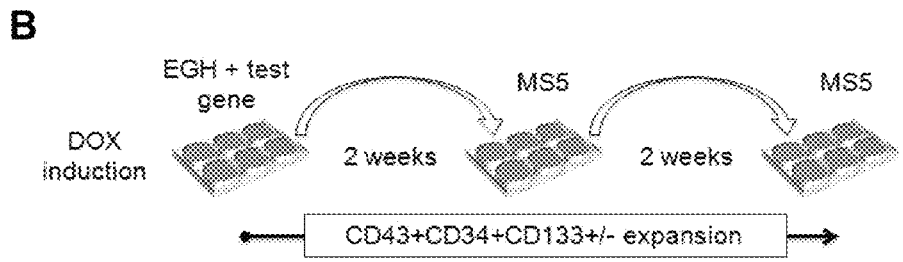
Figure 3C:
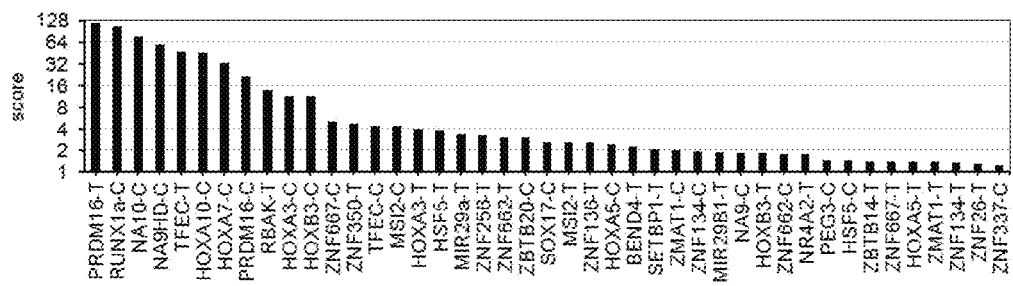

To screen for the additional genes, rtTET-expressing PSCs were transfected with pTight-EGH (blasticidin resistance) and one additional pTight- or pCMV-test gene (geneticin resistance) in PiggyBac expression vectors. EGH and test gene co-expression in transfected cells was achieved by combined blasticidin+geneticin selection. Human PSCs transfected with EGH and test genes were induced 8 days by DOX to produce $CD43^+$ cells and then further expanded in 2 successive 2-week MS5 co-cultures (FIG. 3B). For each test gene, the production of total and primitive hematopoietic cell populations throughout expansion cultures was calculated and expressed as a fraction of internal EGH control. Screening results for genes demonstrating a positive effect on the expansion of EGH-induced primitive progenitors are shown in FIG. 3C. It was found that the addition of HOXA10 driven by the cytomegalovirus (CMV) promoter, which allowed transgene expression after day 8, to ETV2/ERG, GATA2 and HOXA9, greatly improved the proliferation of induced cells during a two-week expansion culture on MS-5 stromal feeder cells and the generation of CD43+CD34+CD133+ cells (FIG. 3A).

Figure 4A:
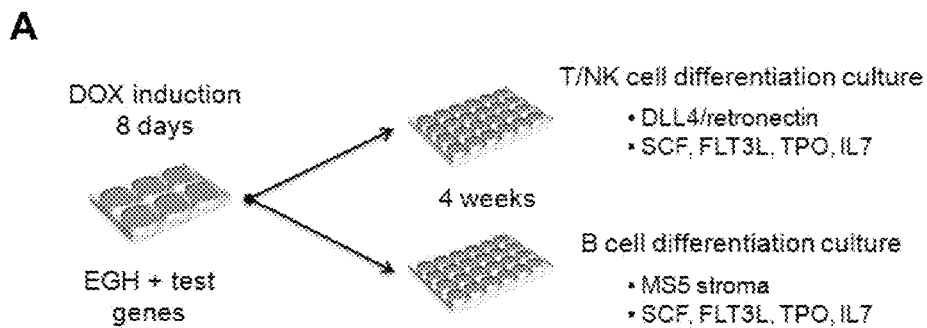
FIGS. 4A-4B: Lymphoid differentiation potential of EGH-induced cells. (A) Schematic of screening model devised to detect genes that improve lymphoid cell development from EGH-induced cells. (B) Flow cytometry analysis of 4 week T/NK and B cell differentiation cultures.
Figure 4B:
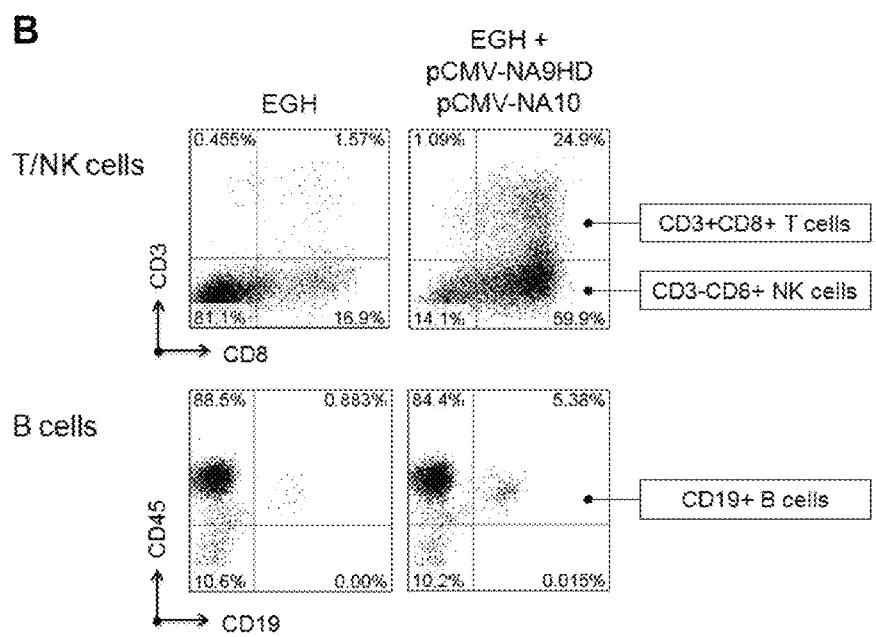

Next, a screening model was devised to detect genes that improve lymphoid cell development from EGH-induced cells (FIG. 4A). For T/NK cells, day 8-induced cells transfected with EGH and test gene combinations were plated in DLL4-Fc/retronectin-coated plates (0.5 µg/cm$^2$ each) at $5\times10^3$ cells/cm$^2$ in T/NK differentiation medium (e.g., StemSpan SFEM (Stem Cell Technologies) supplemented with ascorbic acid, magnesium phosphate (95 µM), Glutamax (1/100; Gibco), Penicillin/Streptomycin (1/100; Gibco) and cytokines—SCF, FLT3L, TPO and IL7 (50 ng/ml each)). Cultures were maintained in hypoxic (e.g., 5% $O_2$) conditions with a half volume medium change every 2 or 3 days. After 2 weeks, the cells were transferred onto fresh DLL4-Fc/retronectin-coated plates for 2 additional weeks. Cells harvested after 4 weeks were analyzed by flow cytometry for CD3$^+$CD8$^+$ T cells and CD3$^-$CD8$^+$ NK cells. For B cells, day 8-induced cells transfected with EGH and test gene combinations were plated on mitomycin C-treated MS5 monolayers at 10$^3$ cells/cm$^2$ in B cell differentiation medium (e.g., IMDM supplemented with FBS (10%, HyClone), Glutamax (1/100, Gibco), Penicillin/Streptomycin (1/100; Gibco), monothioglycerol (100 µM) and cytokines—SCF, FLT3L, TPO (50 ng/ml each), IL7 (20 ng/ml) and IL3 (10 ng/ml), added only at cell plating; or e.g., DMEM-F12 supplemented with FBS (10%, HyClone), Glutamax (1/100, Gibco), Penicillin/Streptomycin (1/100; Gibco), Ascorbic acid (95 µM) and cytokines—SCF and FLT3L (50 ng/ml each), IL7 (20 ng/ml, added only for the first 2 weeks of B cell culture) and IL3 (10 ng/ml, added only for the first week of B cell culture). Cultures were maintained 4 weeks with a half volume medium change every 2 or 3 days. At each feeding with fresh medium, floating non-adherent cells were suspended and removed with medium. Cells harvested after 4 weeks were analyzed by flow cytometry for CD45$^-$CD19$^+$ B cells. It was found that a combination of EGH, pCMV-NA9HD (NUP98-HOXA9 homeodomain fusion protein), and pCMV-NA10 (NUP98-HOXA10 fusion protein) genes enabled efficient differentiation to T, NK and B cells (FIG. 4B).

Example 3

Figure 5A:
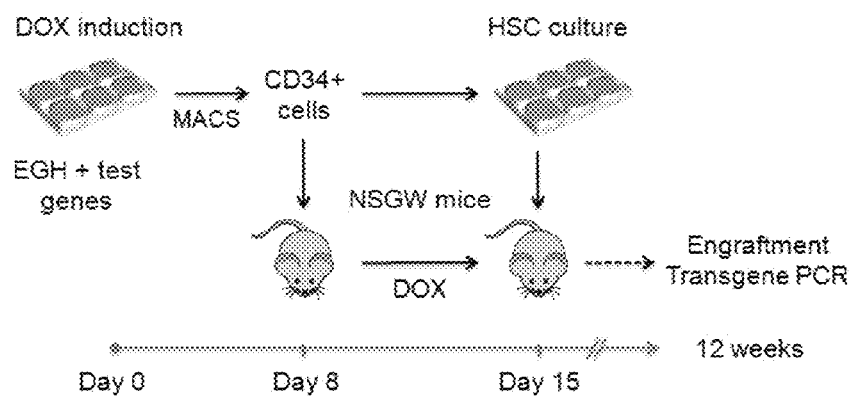
FIGS. 5A-5C: Engraftment potential of EGH-induced cells. (A) Schematic of screening model devised to detect EGH-complementary genes enabling hematopoietic engraftment in immunocompromised mice. (B) Human hematopoietic $CD45^+$ cell detection in peripheral blood and bone marrow of NBSGW mice 12 weeks post injection is shown. (C) Human hematopoietic $CD43/45^-$ cell detection in peripheral blood and bone marrow of NB SGW mice 12 weeks post injection is shown.

Hematopoietic Stem Cell Programming Genes Confer Long-Term Engraftment Potential A screening model was devised to detect hematopoietic stem cell programming genes that can be combined with the EGH expression vector to enable long-term hematopoietic engraftment. CD34$^+$ cells transfected with EGH and different test gene combinations (e.g., up to 20 genes per combination) were purified from day 8 DOX induction cultures by magnet-activated cell sorting (MACS) (FIG. 5A). For immediate post-induction injection, $4\times10^6$ CD34$^+$ cells were plated in recovery culture at 10$^6$ cells/ml in HSC medium (e.g., StemSpan SFEM supplemented with SCF, FLT3L and TPO (100 ng/ml each)), harvested after 18-24 hours and injected intravenously in 6-8 week old NOD/SCID/IL2Rg$^-$/c-kit$^{W41}$ (NBSGW) mice. Injected mice were then placed in cages with DOX-containing diet (i.e., 625 mg DOX/kg) to provide DOX supply for continuous transgene expression in vivo for 7 days. For injection of the HSC culture adapted cells, $0.5\times10^6$ CD34$^+$ cells were plated at $0.2\times10^6$ cells/ml on DLL4-Fc/retronectin-coated plates in HSC medium and cultured for 7 days in hypoxic (e.g., 5% $O_2$) conditions with a half culture volume change on day 4. After culture, harvested cells were injected into the same mice previously injected with day 8 CD34$^+$ cells and fed with DOX-containing diet for 7 days. After injection, mice were transferred on normal diet without DOX and tested for the presence of human hematopoietic (i.e., CD45$^+$HLA Class1$^{30}$) cells in peripheral blood at 6, 12 and 18 weeks, and bone marrow at 20-24 weeks.

Figure 5B:
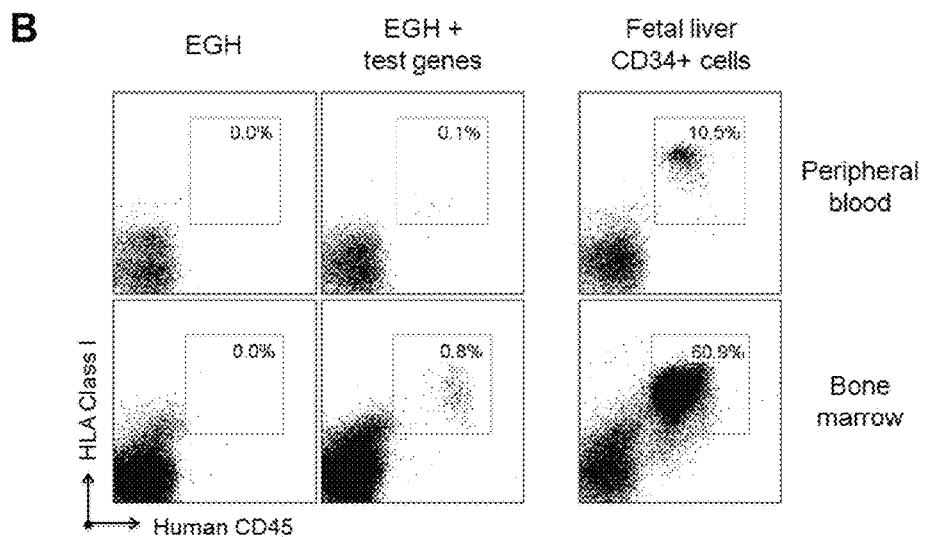
Figure 5C:
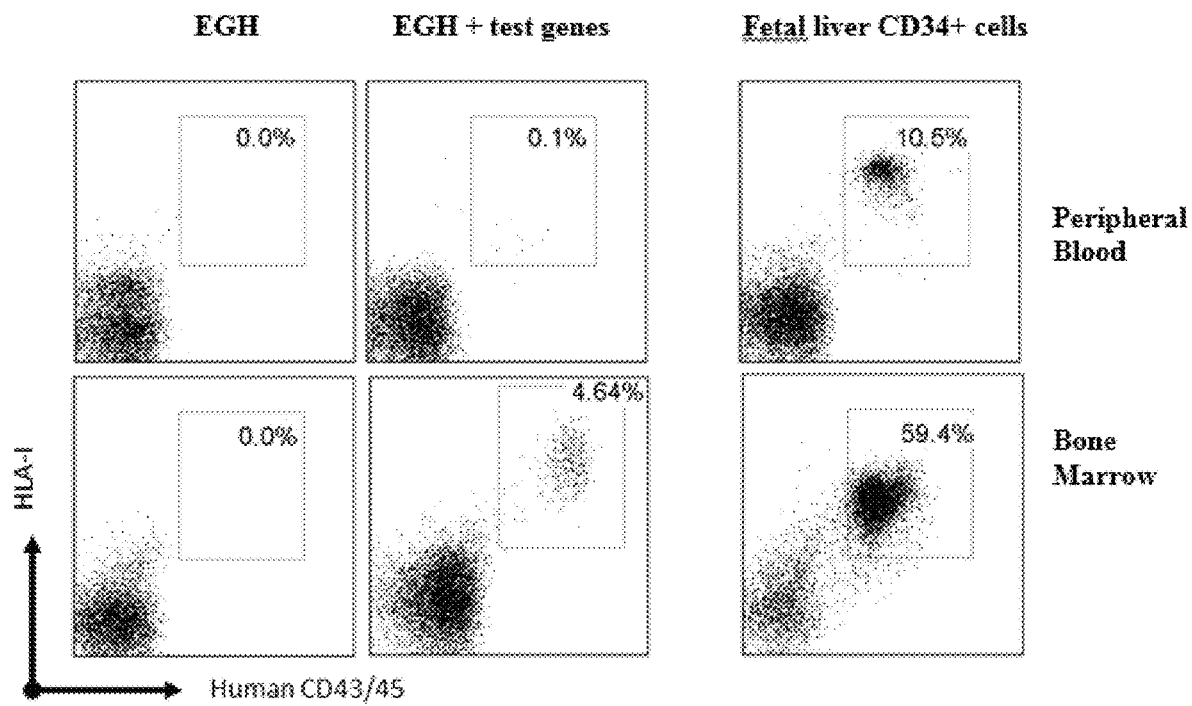

Human hematopoietic CD45$^+$ cells were detected in the peripheral blood and bone marrow of NBSGW mice 12 weeks post injection (FIG. 5B). Human CD45$^+$ cells were not detected in mice injected with EGH-induced cells, whereas EGH in combination with an additional 10 programming genes (Table 1) resulted in detectable human CD45$^+$ cells in peripheral blood and bone marrow. Further analysis was performed for detection of CD43/45$^+$ cells in the mouse bone marrow and peripheral blood of the NBSGW mice 12 week post injection. These CD43/45$^+$ cells were not detected in mice injected with EGH-induced cells, whereas EGH in combination with the additional programming genes resulted in 4.64% CD43/45$^+$ cells in the mouse bone marrow (FIG. 5C).

Figure 6:
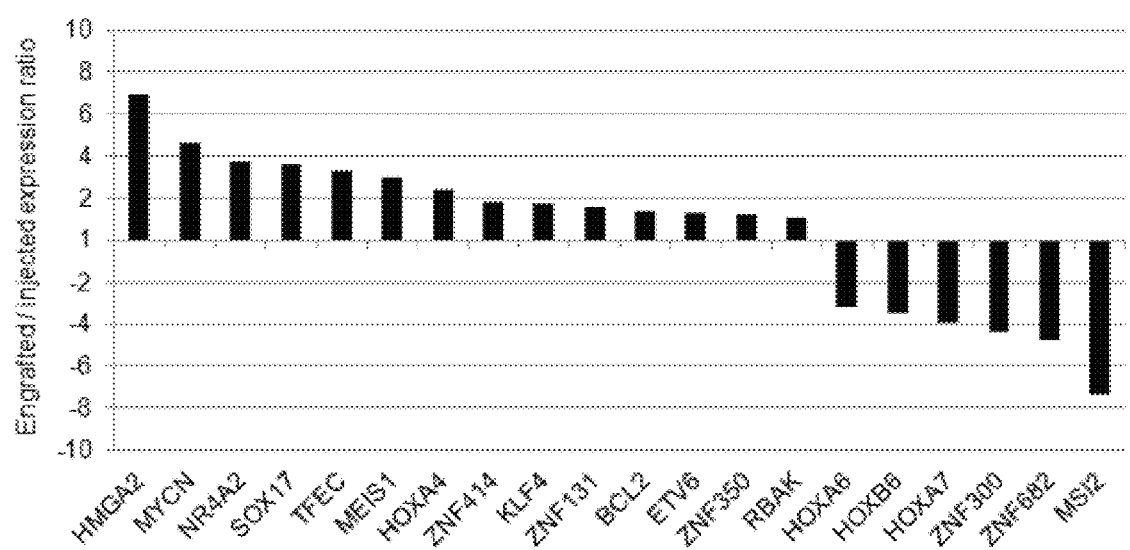
FIG. 6: Graph showing a ratio of transgene expression in engrafted versus injected cells. Respective engrafted/injected expression ratios show enrichment (positive values) or depletion (negative values) of transgenes following cell transplantation.

Next, H1-A16-TET ESCs were co-transfected with hematopoietic inductive EGH genes (blasticidin selection vector) and various combinations of test genes for HSC programming (G418 selection vectors). Transfected ESCs were cultured 2 passages in the presence of blasticidin and G418 to select double transfectants (EGH+test gene combinations), then induced to CD34$^+$ cells and tested for engraftment in NSGW mice as described in FIG. 5A. Expression of each tested transgene in the engrafted mouse bone marrow samples was analyzed by transgene-specific qPCR normalized to the total transgenic cell population detected by EGH-specific primers. This expression was compared to the initial transgene expression in the injected CD34$^+$ cells. Respective engrafted/injected expression ratios show enrichment (positive values) or depletion (negative values) of transgenes following cell transplantation (FIG. 6).

Forty candidate HSC programming genes selected from the preliminary in vitro screening were tested in 3 independent transplantation experiments (using pCMV expression vectors). In total, twenty human transgenes were detected in the bone marrow of engrafted mice at more than 12 weeks after cell injections. As shown in FIG. 6, expression levels of some transgenes in the bone marrow were significantly higher or lower comparing to the injected CD34$^+$ cells indicating in vivo selection of transplantable cells. Regardless of expression levels, however, all detected human genes may contribute to the migration, survival and persistence of PSC-derived CD34$^+$ cells in the bone marrow environment, a known feature of engraftable hematopoietic stem/progenitor cells.

Thus, using a combinational screening strategy in NBSGW mice (McIntosh et al., 2015), hematopoietic stem cell programming genes that confer long-term engraftment of human PSC-derived cells in bone marrow and peripheral blood were identified.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

European Patent No. EP1507865
European Patent No. EP0412700
U.S. Pat. No. 4,683,202
U.S. Pat. No. 5,030,015
U.S. Pat. No. 5,302,523
U.S. Pat. No. 5,322,783
U.S. Pat. No. 5,384,253
U.S. Pat. No. 5,460,964
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,556,954
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,635,387
U.S. Pat. No. 5,656,610
U.S. Pat. No. 5,677,136
U.S. Pat. No. 5,681,599
U.S. Pat. No. 5,702,932
U.S. Pat. No. 5,716,827
U.S. Pat. No. 5,736,396
U.S. Pat. No. 5,736,524
U.S. Pat. No. 5,750,397
U.S. Pat. No. 5,759,793
U.S. Pat. No. 5,780,448
U.S. Pat. No. 5,789,215
U.S. Pat. No. 5,811,094
U.S. Pat. No. 5,827,735
U.S. Pat. No. 5,827,740
U.S. Pat. No. 5,837,539
U.S. Pat. No. 5,837,670
U.S. Pat. No. 5,843,780
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,184,038
U.S. Pat. No. 6,200,806
U.S. Pat. No. 6,833,269
U.S. Pat. No. 6,991,897
U.S. Pat. No. 7,015,037
U.S. Pat. No. 7,029,913
U.S. Pat. No. 7,399,632
U.S. Pat. No. 7,410,773
U.S. Pat. No. 7,410,798
U.S. Pat. No. 7,422,736
U.S. Pat. No. 8,741,648
U.S. Pat. Publn. 2002/0055144
U.S. Pat. Publn. 2002/0102265
U.S. Pat. Publn. 2003/0040038
U.S. Pat. Publn. 2003/0082561
U.S. Pat. Publn. 2003/0211603
U.S. Pat. Publn. 2004/0235175
U.S. Pat. Publn. 2007/0072295
U.S. Pat. Publn. 2007/0116690
U.S. Pat. Publn. 2007/0238170
U.S. Pat. Publn. 2008/0260706
U.S. Pat. Publn. 2009/0148425
U.S. application Ser. No. 08/464,599
U.S. application Ser. No. 61/058,858
U.S. application Ser. No. 61/172,079
U.S. application Ser. No. 61/184,546
Alexander et al., *Proc. Nat. Acad. Sci. USA*, 85:5092-5096, 1988.
Alison et al, *Hepatol.*, 29:678-83, 1998.
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Asoh et al., *Proc. Natl. Acad. Sci. USA*, 99(26):17107-12, 2002.
Ausubel et al., *Current Protocols in Molecular Biology*, Greene Publ. Assoc. Inc. & John Wiley & Sons, Inc., MA, 1996.
Ausubel et al., In: *Current Protocols in Molecular Biology*, John, Wiley & Sons, Inc, New York, 1994.
Batta et al., *Cell Rep.* 2014.
Blomer et al., *J. Virol.*, 71(9):6641-6649, 1997.
Boczkowski et al., *Cancer Res.*, 60:1028-1034, 2001.
Boyer et al., *Cell*, 122(6):947-56, 2005.
Buss et al., *Mol. Cell. Biol.*, 8:3960-3963, 1988.
Byrne et al., *Nature*, 450(7169):497-502, 2007.
Capecchi, *Nature*, 348(6297):109, 1990.
Cassiede et al., *J. Bone Miner. Res.*, 11(9):1264-1273, 1996.
Cermak et al., *Nucleic Acids Res.*, 39(17):7879, 2011.
Chambers et al., *Cell*, 113(5):643-55, 2003.
Chen and Okayama, *Mol. Cell Biol.*, 7(8):2745-2752, 1987.
Chevalier et al., *Prostaglandins Other Lipid Mediat.*, 70(1-2):31-37, 2002.
Christian et al., *Genetics*, 186(2):757-761, 2010.
*Current Protocols in Stem Cell Biology*, Bhatia et. al. (Ed.), John Wiley and Sons, Inc., 2007.
Derossi et al., *J. Bio. Chem.*, 269:10444-10450, 1994.
Derossi et al., *J. Biol. Chem.*, 271:18188, 1996.
Derossi et al., *Trends in Cell Biol.*, 8:84-87, 1998.
Doulatov et al., *Cell Stem Cell* 13(4): 459-470, 2013.
Durai et al., *Nucleic Acids Res.*, 33(18):5978-5990, 2005.
Elango et al., *Biochem. Biophys. Res. Comm.*, 330:958-966, 2005.
Elcheva et al., *Nat Commun* 5: 4372, 2014.
Elliott and O'Hare, *Cell*, 88:223-234, 1997.
Ercolani et al., *J. Biol. Chem.*, 263:15335-15341, 1988.
Evans, et al., In: *Cancer Principles and Practice of Oncology*, Devita et al. (Eds.), Lippincot-Raven, NY, 1054-1087, 1997.
Fawell et al., *Proc. Natl. Acad. Sci. USA*, 91:664-668, 1994.
Fechheimer et al., *Proc Natl. Acad. Sci. USA*, 84:8463-8467, 1987.

Fraley et al., *Proc. Natl. Acad. Sci. USA*, 76:3348-3352, 1979.
Frankel and Pabo, *Cell*, 55(6):1189-1193, 1988.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gopal, *Mol. Cell Biol.*, 5:1188-1190, 1985.
Graham and Van Der Eb, *Virology*, 52:456-467, 1973.
Gronthos, *Blood*, 84(12):41644173, 1994.
Hancock et al., *EMBO J.*, 10:4033-4039, 1991.
Harland and Weintraub, *J. Cell Biol.*, 101(3):1094-1099, 1985.
Hill et al., *Exp. Hematol.*, 24(8):936-943, 1996.
Ho et al., *Cancer Res.*, 61(2):474-7, 2001.
In vitro *Methods in Pharmaceutical Research*, Academic Press, 1997.
Jaiswal et al., *J. Cell Biochem.*, 64(2):295-312, 1997.
Johnstone et al., 238(1):265-272, 1998.
Kaeppler et al., *Plant Cell Rep.*, 8:415-418, 1990.
Kaneda et al., *Science*, 243:375-378, 1989.
Karin et al. *Cell*, 36: 371-379, 1989.
Kato et al, *J. Biol. Chem.*, 266:3361-3364, 1991.
Kilic et al., *Stroke*, 34:1304-10, 2003.
Kirchmaier and Sugden, *J. Virol.*, 72(6):4657-4666, 1998.
Kitajima et al., *Blood*, 2011.
Klein et al., *Nature*, 327:70-73, 1987.
Kyba et al., *Cell* 109(1): 29-37, 2002.
Langle-Rouault et al., *J. Virol.*, 72(7):6181-6185, 1998.
Levitskaya et al., *Proc. Natl. Acad. Sci. USA*, 94(23):12616-12621, 1997.
Li et al., *Nucleic Acids Res.*, 39(14):6315-6325, 2011.
Lindgren et al., *Trends in Pharmacol. Sci.*, 21:99-103, 2000.
Lindner et. al., *J. Virol.*, 82(12):5693-702, 2008.
Macejak and Sarnow, *Nature*, 353:90-94, 1991.
Makino et al., *J. Clin. Invest.*, 103(5):697-705, 1999.
Maniatis, et al., *Molecular Cloning, A Laboratory Manual*, Cold Spring Harbor Press, Cold Spring Harbor, N.Y., 1988.
Mann and Frankel, *EMBO J.*, 1, 10:1733-1739, 1991.
Mann et al., *Cell*, 33:153-159, 1983.
McIntosh et al., *Stem Cell Reports*, 2015.
Miller et al., *Am. J Clin. Oncol.*, 15(3):216-221, 1992.
Miller et al., *Nat. Biotechnol.*, 29(2):143-148, 2011.
Minskaia and Ryan, *BioMed Research International*, 291730, 2013.
Nabel et al., *Science*, 244(4910):1342-1344, 1989.
Naldini et al., *Science*, 272(5259):263-267, 1996.
Ng, *Nuc. Acid Res.*, 17:601-615, 1989.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Oberlin et al., *Int. I Dev. Biol. Sci.*, 54:1165, 2010.
Paskind et al., *Virology*, 67:242-248, 1975.
PCT Appln. PCT/IB2010/000154
PCT Appln. WO 03/042405
PCT Appln. WO 03/059940
PCT Appln. WO 03/059941
PCT Appln. WO 94/09699
PCT Appln. WO 95/06128
PCT Appln. WO 96/39487
PCT Appln. WO 99/20741
Pelletier and Sonenberg, *Nature*, 334:320-325, 1988.
Pereira et al., *Cell Stem Cell*, 2013.
Pimanda and Gottgens, *Int J. Dev. Biol. Sci.*, 54:1201, 2010.
Pingoud and Silva, *Nat. Biotechnol.*, 25(7):743-744, 2007.
Potrykus et al., *Mol. Gen. Genet.*, 199(2):169-177, 1985.
Potten, *Philos. Trans. R Soc. Lond. B Biol. Sci.*, 353:821-30, 1998.
Potter et al., *Proc. Natl. Acad. Sci. USA*, 81:7161-7165, 1984.
Quitsche et al., *J. Biol. Chem.*, 264:9539-9545, 1989.
Reubinoff et al., *Nat. Biotechnol.*, 18:399B404, 2000.
Richards et al., *Cell*, 37: 263-272, 1984.
Riddell et al., *Cell* 157(3): 549-564, 2014.
Rippe et al., *Mol. Cell Biol.*, 10:689-695, 1990.
Rothbard et al., *Nat. Med.*, 6(11):1253-7, 2000.
Sambrook and Russell, *Molecular Cloning: A Laboratory Manual*, 3$^{rd}$ Ed. Cold Spring Harbor Lab. Press, 2001.
Sambrook et al., *Molecular Cloning: A Laboratory Manual*, Vol. 1, Cold Spring Harbor Laboratory Press, Cold Spring Harbor, N.Y., (7)7:19-17.29, 1989.
Sandler et al., *Nature* 511(7509): 312-318, 2014.
Schwarze et al., *Science*, 285(5433):1466-7, 1999.
Schwarze et al., *Science*, 285:1569-1572, 1999.
Seaboe-Larssen et al., *J. Imm. Methods*, 259:191-203. 2002.
Silva et al., *Curr. Gene Ther.*, 11(1):11-27, 2011.
Smith, In: *Origins and Properties of Mouse Embryonic Stem Cells, Annu. Rev. Cell. Dev. Biol.*, 2000.
Suzuki et al. *Mol Ther*, 2013.
Takahashi and Yamanaka, *Cell*, 126:663-676, 2006.
Takahashi et al., *Cell*, 126(4):663-76, 2007.
Takahashi et al., *Cell*, 131:861-872, 2007.
Tanaka et al., *J. Immunol.*, 170(3):1291-8, 2003.
Temin, In: *Gene Transfer*, Kucherlapati (Ed.), NY, Plenum Press, 149-188, 1986.
Thomson and Marshall, *Curr. Top. Dev. Biol.*, 38:133-165, 1998.
Thomson and Odorico, *J. Trends. Biotechnol.*, 18:53B57, 2000.
Thomson et al. *Proc. Natl. Acad. Scie. USA*, 92:7844-7848, 1995.
Thomson et al., *Science*, 282:1145, 1998.
Tur-Kaspa et al., *Mol. Cell Biol.*, 6:716-718, 1986.
Vodyanik et al., *Blood*, 108:2095, 2006.
Walsh et al., *Immunity*, 17:665, 2002.
Watt, *Philos. Trans. R. Soc. Lond. B. Biol. Sci.*, 353:831, 1997.
Weber et al., *PLoS One*, 6(5):e19722, 2011.
Wender et al., *Proc. Natl. Acad. Sci. USA*, 97(24):13003-8, 2000.
Wilson et al., *Blood*, 113:5456, 2009.
Wilson et al., *Mol. Cell Biol.*, 30:3853, 2010.
Wilson et al., *Science*, 244:1344-1346, 1989.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Xu et al., *Nat. Biotechnol.*, 19:971-974, 2001.
Yang and Russell, *Proc. Natl. Acad. Sci. USA*, 87:4144-4148, 1990.
Ying et al., *Cell*, 115:281-292, 2003.
Yoo et al., *J. Bone Joint Sure. Am.*, 80(12):1745-1757, 1998.
Yu and Thompson, *Genes Dev.*, 22(15):1987-97, 2008.
Yu et al., *Science*, 318:1917-1920, 2007.
Yu et al., *Science*, 324(5928):797-801, 2009.
Zhang et al., *Nat. Biotechnol.*, 29(2):149-153, 2011.
Zufferey et al., *Nat. Biotechnol.*, 15(9):871-875, 1997.

What is claimed is:

1. An in vitro method for producing hematopoietic precursor cells from pluripotent stem cells comprising:
 (a) providing pluripotent stem cells (PSCs) comprising at least one expression construct encoding hematopoietic precursor programming genes, wherein the hematopoietic precursor programming genes comprise ETS/ERG, GATA2, and HOXA9 genes co-expressed;
(b) culturing the PSCs wherein the PSCs are induced to express the hematopoietic precursor programming genes, thereby producing hematopoietic precursor cells (HPCs); and
(c) further culturing the HPCs, wherein expression of the hematopoietic precursor programming genes is no longer induced, to produce a population of cells comprising at least 70% multi-lineage HPCs with expression of CD34 and CD43.

2. The method of claim 1, wherein the multi-lineage HPCs are capable of differentiating into myeloid and lymphoid lineages.

3. The method of claim 1, wherein the expression construct is a transposon- or episomal-based expression construct.

4. The method of claim 1, wherein the hematopoietic precursor programming genes are under the control of a single promoter.

5. The method of claim 4, wherein the single promoter is an inducible promoter.

6. The method of claim 5, wherein the inducible promoter is a tetracycline-inducible promoter.

7. The method of claim 1, wherein the culturing of step (b) is about four to about ten days.

8. The method of claim 1, wherein the pluripotent stem cells are embryonic stem cells (ESCs) or induced pluripotent stem cells (iPSCs).

9. The method of claim 1, wherein the pluripotent stem cells are human pluripotent stem cells.

10. The method of claim 1, wherein the multi-lineage HPCs further express one or more hematopoietic precursor markers in addition to the CD34 and the CD43.

11. The method of claim 10, wherein the one or more hematopoietic precursor markers are selected from the group consisting CD33, CD45, CD235a, and CD41a.

12. The method of claim 10, wherein the one or more hematopoietic precursor markers is CD45.

13. The method of claim 1, wherein the multi-lineage HPCs are immature HPCs.

14. The method of claim 13, wherein at least 90 percent of the multi-lineage HPCs are immature HPCs.

15. The method of claim 1, wherein the HPCs of step (c) are cultured in the absence of stromal cells.

16. The method of claim 1, wherein the HPCs of step (c) are cultured in serum free or defined medium.

17. The method of claim 15, wherein the multi-lineage HPCs can be differentiated into two or more cell types selected from the group consisting of plasma cell, natural killer cell, macrophage, mast cell, megakaryocyte, erythrocyte, granulocyte, lymphocyte, monocyte, leukocyte, and thrombocyte.

18. The method of claim 17, wherein the lymphocyte is a B lymphocyte and/or a T lymphocyte.

19. The method of claim 1, wherein the ETS/ERG gene is ERG (v-ets erythroblastosis virus E26 oncogene homolog), ETV2 (ets variant 2), FLI-1 (Friend leukemia virus integration 1), ELK3 (ETS domain-containing protein), ETS1 (C-ets-1), or ETS2 (C-ets-2).

20. The method of claim 1, wherein the ETS/ERG gene is ERG or ETV2.

21. The method of claim 1, wherein the hematopoietic precursor programming genes are fused to a targeting sequence.

22. The method of claim 21, wherein the targeting sequence is NUP98 or a homeodomain thereof.

23. The method of claim 1, wherein the hematopoietic precursor programming genes comprise ERG, GATA2, HOXA9, NUP98-HOXA9 and NUP98-HOXA10.

24. The method of claim 1, wherein the hematopoietic precursor programming genes comprise ETV2, GATA2, HOXA9, NUP98-HOXA9 and NUP98-HOXA10.

25. The method of claim 1, wherein the PSCs of step (a) further comprise at least one additional expression construct encoding one or more hematopoietic stem cell programming genes.

26. The method of claim 25, wherein the one or more hematopoietic stem cell programming genes are selected from the group consisting of BCL2, BEND4, BMI1, CIITA, EGR3, ETV6, EZH1, EZH2, FOXL1, HIF3A, HLF, HMGA2, HOXA10, HOXA3, HOXA4, HOXA5, HOXA6, HOXA7, HOXB3, HOXB6, HSF5, KLF2, KLF4, MECOM, MEIS1, MIR29A, MIR29B1, MSI2, MYB, MYCN, NKX2-3, NR4A2, PEG3, PRDM12, PRDM16, RBAK, RUNX1, RUNX3, SETBP1, SOX17, SOX8, TFEC, ZBTB14, ZBTB20, ZMAT1, ZNF131, ZNF134, ZNF136, ZNF256, ZNF26, ZNF300, ZNF337, ZNF350, ZNF414, ZNF662, ZNF667 and ZNF682.

27. The method of claim 25, wherein expression of the one or more hematopoietic stem cell programming genes is constitutive in the HPCs of step (b).

28. The method of claim 25, wherein expression of the one or more hematopoietic stem cell programming genes is essentially silenced in the pluripotent stem cells.

29. The method of claim 25, wherein the hematopoietic stem cell programming genes are fused to a targeting sequence.

30. The method of claim 29, wherein the targeting sequence is NUP98 or a homeodomain thereof.

31. An in vitro method for producing hematopoietic precursor cells from pluripotent stem cells comprising:
(a) providing pluripotent stem cells (PSCs) comprising an expression construct encoding ERG, GATA2, and HOXA9 under the control of a single promoter; and
(b) culturing the pluripotent stem cells with coexpression of ERG, GATA2, and HOXA9, thereby producing hematopoietic precursor cells (HPCs); and
(c) further culturing the HPCs without coexpression of ERG, GATA2, and HOXA9, to produce a population of cells comprising at least 70% multi-lineage HPCs with expression of CD34 and CD43.

32. The method of claim 5, wherein the inducible promoter is a bi-directional Tight promoter.

33. The method of claim 1, wherein the ETS/ERG, GATA2, and/or HOXA9 genes are linked through a 2A-cleavage peptide.

34. The method of claim 1, further comprising step (d) differentiating the HPCs to myeloid lineage cells or lymphoid lineage cells.

35. The method of claim 6, wherein the PSCs are cultured in the presence of 0.25 μg/mL doxycycline for induction of gene expression in step (b).

* * * * *